(12) United States Patent
Stenger-Smith et al.

(10) Patent No.: US 8,427,812 B1
(45) Date of Patent: Apr. 23, 2013

(54) ELECTROACTIVE POLYMER BASED SUPERCAPACITORS INCLUDING A CATHODE HAVING BBL OR PRY-BBL

(75) Inventors: John D. Stenger-Smith, Ridgecrest, CA (US); Jennifer A. Irvin, San Marcos, TX (US); David J. Irvin, San Marcos, TX (US); William Lai, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 259 days.

(21) Appl. No.: 12/898,288

(22) Filed: Oct. 5, 2010

Related U.S. Application Data

(63) Continuation-in-part of application No. 12/178,972, filed on Jul. 24, 2008, now Pat. No. 7,829,660.

(51) Int. Cl.
*H01G 9/00* (2006.01)
*H01G 9/04* (2006.01)
*H01G 9/145* (2006.01)

(52) U.S. Cl.
USPC .............. 361/502; 361/516; 361/532; 546/41

(58) Field of Classification Search ...................... 546/41
See application file for complete search history.

(56) References Cited

U.S. PATENT DOCUMENTS

| | | | |
|---|---|---|---|
| 6,965,509 B2 * | 11/2005 | Reynolds et al. | 361/528 |
| 7,608,179 B1 | 10/2009 | Irvin et al. | |
| 2010/0172011 A1 * | 7/2010 | Piroux et al. | 359/268 |
| 2011/0045357 A1 * | 2/2011 | Saito et al. | 429/303 |

OTHER PUBLICATIONS

Poly(popylenedioxy)thiophene-based supercapacitors operating a low temperatures, Journal of the electrical society, 157, (3) A298-A304(2010).
Stenger-Smith, et al, J. of the electrochemical society, 149(8) A973-A977 (2002).
Stenger-Smith et al, J. of the electrochemical society, 157(3) A298-A304 (2010).
Witker, et al, J. of the electrochemical society, 154(4) G95-G98 (2007).
Irvin, et al, Polymer preprints 2007, 48(2) 150.

\* cited by examiner

*Primary Examiner* — Jayprakash N Gandhi
*Assistant Examiner* — Dion Ferguson
(74) *Attorney, Agent, or Firm* — Charlene A. Haley

(57) ABSTRACT

A process used to cast films including: mixing BBL and a room temperature molten salt from a range of about 35:65 weight ratio, dissolving the mixture in about 1% methanesulfonic acid to produce a BBL solution, drop casting the solution onto glass or gold coated glass at 140° C. in air and heating for about 2 hours to produce films, drying the films in a vacuum oven at about 100° C. for at least 24 hours under dynamic vacuum, and rinsing the films to remove residual ionic liquid.

15 Claims, 13 Drawing Sheets ns below −65° C.

BACKGROUND OF THE INVENTION

Electroactive polymer devices, in which the polymers switch between redox states to store charge, have been the object of concentrated research over the past several years. As these polymers have the possibility of being switched between their neutral form, a p-type doped oxidized form, and an n-type doped reduced form, a variety of electrode configurations are possible. This has been exemplified by the use of electroactive polymers in supercapacitors, rechargeable storage batteries, and electrochromic devices. S. Gottesfeld, J. P. Ferraris, A. Rudge, and I. Raistrick, *Electrochim. Acta*, 39, 273, (1994). 2. P. Novák, K. Müller, K. S. V. Santhanam, and O. Haas, *Chem. Rev.* (Washington, D.C.), 97, 207-281 (1997). 3. P. M. S. Monk, R. J. Mortimer, and D. R. Rosseinsky, *Electrochromism: Fundamentals and Applications*, VCH, Weinheim (1995). 4. S. A. Sapp, G. A. Sotzing, and J. R. Reynolds, *Chem. Mater.*, 10, 2101 (1998). The poly(3,4-alkylenedioxythiophenes) (PXDOTs) have especially useful redox switching properties due to their electron-rich character, which yields especially low switching potentials. L. B. Groenendaal, F. Jones, D. Freitag, H. Pielartzik, and J. R. Reynolds, *Adv. Mater.*, 12, 481 (2000). The parent polymer of this family, poly(3,4-ethylenedioxythiophene), has now been developed to the point of commercialization (Baytron P, Bayer AG) and is used as a stable conducting material in photographic film, tantalum capacitors, and feedthrough holes in printed circuit boards. S. W. Schneller and J. D. Petru, *Synth. Commun.*, 4, 29 (1992). In addition, these polymers switch rapidly and efficiently between their neutral and p-doped forms with a minimum of side reactions and long switching lifetimes. As such, they have been heavily investigated for a number of redox devices including electrochromic applications. A. L. Dyer and J. R. Reynolds, in *Handbook of Conducting Polymers*, 3rd ed., T. Skotheim and J. R. Reynolds, Editors, Taylor & Francis, Boca Raton, Fla. (2008). Polymeric supercapacitors using PXDOTs as the charge carrying layer exhibit excellent reversibility and coulombic efficiency. J. D. Stenger-Smith, C. K. Webber, N. A. Anderson, A. P. Chafin, K. Zong, and J. R. Reynolds, *J. Electrochem. Soc.*, 149, A973 (2002). J. D. Stenger-Smith, J. A. Irvin, D. J. Irvin, T. Steckler, and J. R. Reynolds, *Polym. Mater. Sci. Eng.*, 99, 699 (2008).

It is well known that changes in redox states of electroactive polymers require movement of ions to maintain electroneutrality. Ion choice can affect morphology, stability, and oxidation and reduction potentials. J. A. Irvin, D. J. Irvin, and J. D. Stenger-Smith, in *Handbook of Conducting Polymers*, 3rd ed., T. Skotheim and J. R. Reynolds, Editors, Taylor & Francis, Boca Raton, Fla. (2008). Ions have traditionally been introduced as a solution of molecular electrolyte, commonly a tetraalkylammonium cation with anions such as $ClO_4^-$, $PF_6^-$, and $BF_4^-$; common solvents include water, acetonitrile, and propylene carbonate. Recently ionic liquids such as 1-ethyl-3-methylimidazolium and Bis(trifluoro methanesulfonyl)imide (EMIBTI) have been investigated as electrolytes, either with or without additional solvent. J. D. Stenger-Smith, C. K. Webber, N. A. Anderson, A. P. Chafin, K. Zong, and J., J. M. Pringle, M. Forsyth, D. R. MacFarlane, K. Wagner, S. B. Hall, and D. L. Officer, *Polymer*, 46, 2047 (2005). Ionic liquid electrolytes are advantageous due to their wide temperature use window, low volatility, and good electrochemical and thermal stability. W. Lu, A. G. Fadeev, B. Qi, E. Smela, B. R. Mattes, J. Ding, G. M. Spinks, J. Mazurkiewicz, D. Zhou, G. G. Wallace, et al., *Science*, 297, 983 (2002).

A key component in many electrochromic and other redox switchable devices is the formulation of suitable supporting electrolytes. The electrolyte used in our previous work often consisted of a room-temperature ionic liquid such as EMIBTI. EMIBTI is stable up to 300° C., has an Electrochemical window of 4.3 V, and a melting point of −15° C. J. D. Stenger-Smith, C. K. Webber, N. A. Anderson, A. P. Chafin, K. Zong, and J. R. Reynolds, *J. Electrochem. Soc.*, 149, A973 (2002). 9. J. D. Stenger-Smith, J. A. Irvin, D. J. Irvin, T. Steckler, and J. R. Reynolds, *Polym. Mater. Sci. Eng.*, 99, 699 (2008).

Adding to the challenge to the operation of these devices are conditions required by both civilian and military applications. These conditions typically range from −50 to +50° C. under a variety of humidity conditions. These conditions require that all devices, especially high voltage devices, be hermetically sealed.

The Demand for Low Temperature Operation

With increasing focus on energy production and energy storage, there is an increased need for charge storage devices that operate at a wide variety of temperatures. B. Conway, V. Birss, and E. Wojtowic, *J. Power Sources*, 66, 1 (1997). 14. C. Arbizzani, M. Mastragostino, and B. Scrosati, in *Handbook of Conducting Polymers*, 2nd ed., T. A. Skotheim, R. L. Elsenbaumer, and J. R. Reynolds, Editor, Marcel Dekker, New York (1998). There are many batteries that operate well at room temperature or higher, but there are very few that operate below 0° C., and fewer still operate down to −60° C. P. Novák, K. Müller, K. S. V. Santhanam, and O. Haas, *Chem. Rev.* (Washington, D.C.), 97, 207-281 (1997). C. A. Vincent and B. Scrosati, *Modern Batteries: An Introduction to Electrochemical Power Sources*, pp. 305-310, John Wiley & Sons, New York (1997). Aside from slowing down the actual kinetics of the charge/discharge reaction (oxidation/reduction, for example), lower temperatures also increase the viscosity of electrolytes, lowering the ability of the electrolyte to transfer charge. Furthermore, at low temperatures, electrolyte mixtures containing ionic liquids may become unstable due to crystallization or co-crystallization of ionic liquid components, phase separation, or supersaturation of components that dissolve into the electrolyte at higher temperatures. Such instabilities lead to degradation of device performance or failure upon extended exposure to low temperatures, even if the mixture has not vitrified. Therefore, there is a great need for stable ionic liquids which can support electrochemical operations at low temperatures.

There are very few electrolytes that are liquid below −60° C. and even fewer room-temperature ionic liquids that are liquid below this temperature. J. Y. Song, Y. Y. Wang, and C. C. Wan, *J. Power Sources*, 77, 183 (1997). D. Aurbach, *Electrochim. Acta*, 50, 247 (2004). Adding to the challenge is the fact that these materials must support electrochemical processes at a wide range of temperatures.

It is to be understood that the foregoing is exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

Figure 1:
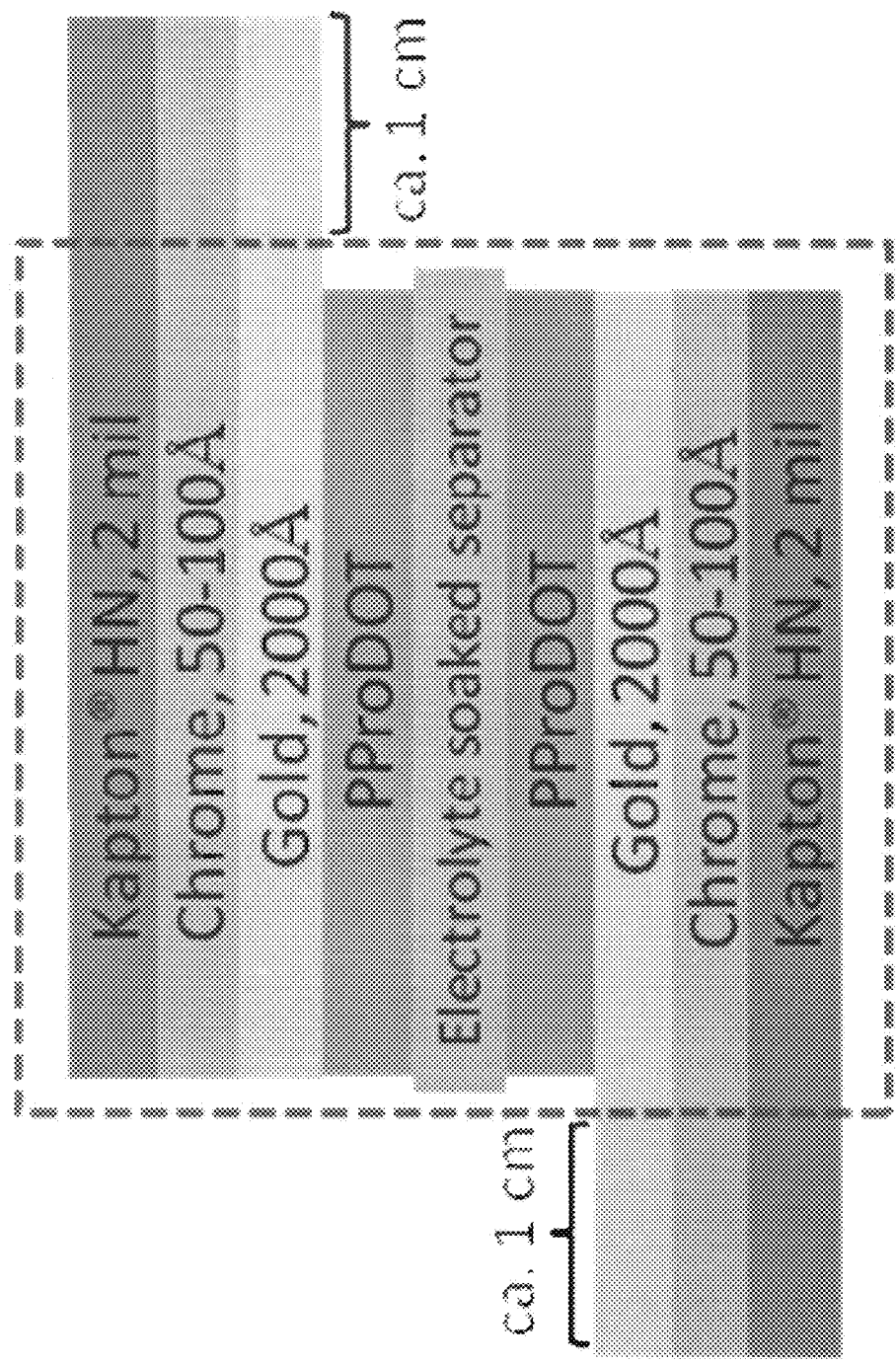
FIG. 1 is a diagram of sealed two-electrode supercapacitor construction, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to supercapacitors, and more specifically, electrolytes formulated to exhibit melt transitions below −65° C.

These new materials and processes will enable electrochemical capacitors, fast polymer batteries and other energy storage devices to operate at MILSPEC ranges (−60 to +60 Celsius). State of the art materials solidify around −20 Celsius. Previously, no materials were available that remain liquid at low temperature, and liquid state is necessary for performance of energy performance devices.

The Navy has several power leveling initiatives and there is a demonstrated need for power sources that can store more energy than capacitors and deliver more power than batteries. Polymer electrochemical capacitors can fill this need. These devices must be able to withstand the temperature extremes listed in military specifications, and it is critical that new low temperature electrolytes be developed for this need and perhaps most importantly, working power storage devices that can withstand these temperatures be constructed and tested.

The ionic liquids used in polymer electrochemical capacitors work extremely well at room temperature and higher, but most ionic liquids to date freeze at or above −20 degrees Celsius. In general, ionic solids tend to be very poor ionic conductors. Embodiments of the invention demonstrate several ionic materials/mixtures that remain liquid below −60 degrees Celsius, and therefore, maintain good ionic conductivity at extended temperature ranges.

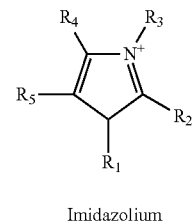

Imidazolium

R1: said substituents selected from the group including of: hydrogen; alkyl of from 1 to about 22 carbon atoms; alkoxy including from 1 to about 22 carbon atoms; nitro; halogen; cyano ester, mono- & di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms.

R2: said substituents selected from the group including of: hydrogen; alkyl of from 1 to about 22 carbon atoms; alkoxy including from 1 to about 22 carbon atoms; nitro; halogen; cyano ester, mono- & di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms.

R3: said substituents selected from the group including of: hydrogen; alkyl of from 1 to about 22 carbon atoms; alkoxy including from 1 to about 22 carbon atoms; nitro; halogen; cyano ester, mono- & di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms.

R4: said substituents selected from the group including of: hydrogen; alkyl of from 1 to about 22 carbon atoms; alkoxy including from 1 to about 22 carbon atoms; nitro; halogen; cyano ester, mono- & di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms.

R5: said substituents selected from the group including of: hydrogen; alkyl of from 1 to about 22 carbon atoms; alkoxy including from 1 to about 22 carbon atoms; nitro; halogen; cyano ester, mono- & di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms.

The initial synthetic targets for the imidazoles are to have R1 be methyl and R2 be ethyl(ethyloxy)methyl (glyme), ethylhexyl, and 1,1,1,2,2-pentafluorobutyl. These choices cover a range of possible intramolecular and intermolecular interactions to decrease the melting points. Anions including tetrafluoroborate ($BF_4^-$), hexafluorophosphate ($PF_6^-$), and bis (trifluoromethyl sulfonyl)imide (BTI) are common to the lowest melting commercial ionic liquids. In this supercapacitor work, BTI was used almost exclusively, and $BF_4^-$ and $PF_6^-$ was tried recently. In an effort to depress the melting points further, eutectic mixtures and blends were tried. The eutectic mixture strategy in other embodiments may also help stabilize the conductivity over a wider temperature range due to decreased viscosity from imperfect packing of ions. Of particular note is the mixture of 1-ethyl-3-methyl imidazolium bis(trifluoromethyl sulfonyl)imide (EMIBTI) and 1-ethyl-3-methyl imidazolium hexafluorophosphate (EMIPF6) which demonstrates liquid state well below −60 Celsius.

Polymer electrochemical capacitors were constructed and analyzed electrochemically in a water- and oxygen-free environment then hermetically sealed. These devices were tested in an environmental chamber at temperatures from approximately −50 to 50 Celsius. The formulation of the electrolyte, the active polymer layers and any hermetic sealing material can be modified to optimize device performance. In some embodiments, mix salts are in various proportions, test salts via thermal analysis are to validate liquid state at MILSPEC ranges.

Embodiments of the invention describe ionic compounds, either single compounds or mixtures thereof, which remain liquids at MILSPEC temperature ranges (−60 to +60 Celsius). Single ionic compounds and/or mixtures of ionic compounds that remain liquids at these temperature ranges can be used in a variety of devices that require ionic conduction.

Potential applications for embodiments include, but are not limited to, low temperature batteries, low temperature supercapacitors, low temperature electrochemical devices, electrochromic windows, low temperature photovoltaic cells, fuel cells, environmentally friendly solvents. The core themes of this work are to test the charge capacity, power density and cycle lifetime of polymer electrochemical capacitors at temperatures from −55 to +55° C. and to synthesize new ionic liquids with melt transitions below −65° C. The ionic liquids used in polymer electrochemical capacitors work extremely well at room temperature and higher, but most ionic liquids to date freeze at or above −40° C.

Several Electrolytes Formulated and Tested with Differential Scanning Calorimetry (DSC)

Objectives were to test the charge capacity, power density and cycle lifetime of polymer electrochemical capacitors at temperatures from −55 to +55° C., and synthesize-formulate new ionic liquids with melt transitions below −65° C. The approach included the test of all new materials versus the standard EMIBTI. Differential Scanning calorimetry to test thermal properties, electrochemical analysis of polymeric supercapacitors (charge, energy density, average power versus frequency and temperature), hermetically seal all cells, and use most reliable polymeric supercapacitor.

Polymeric Supercapacitors

These supercapacitors would include: high power/energy storage, higher power density than batteries (kW/kg), similar operating voltage to batteries (1-3V per cell), shorter operating times than batteries (sec-min), and higher energy density than traditional capacitors (~3 Wh/kg). Applications included, but are not limited to, military (short intense bursts of power), computer backup (less power, longer time), and electric vehicle burst power (intermediate power and length). The materials included, but are not limited to, inorganic oxides (RuO2>720F/g) and electroactive polymers (PPy 350F/g, PANT, PT 250F/g, etc.).

There is a need to demonstrate operation of batteries and capacitors at MILSPEC Temps.

FIG. 1 shows the Charging Process in Electroactive Polymers (Rudge et al., *J. Power Sources* 1994, 47, 89-107.) Observations: higher frequency performance most sensitive to temperature, cell not sealed; electrolyte appears to leak out at high temperature, salt formulation with no thermal transition between −60 and +60 C found (device testing priority), and analysis will be performed to determine whether the synthesis of new materials is necessary.

Several Electrolytes were tested including, but not limited to, EMIBTI: ethyl methyl imidazolium bis(trifluoromethyl sulfonyl)imide, TEABTI: tetraethyl ammonium bis(trifluoromethyl sulfonyl)imide, TBAP: tetrabutyl ammonium perchlorate —$[N(C_4H_9)_4]^+$−$[ClO_4]$, EMIMS: ethyl methyl imidazolium methane sulfonate, polyetherlBTI: 1-(methoxyethoxyethane)-2-methyl imidazolium bis(trifluoromethyl sulfonyl)imide, BTI: bis(trifluoromethyl sulfonyl) imide, $BF_4^-$: tetrafluoroborate, boron tetrafluoride, $PF_6^-$ hexafluorophosphate, phosphorous hexafluoride.

Several Electrolytes Formulated and Tested with DSC

| Formula | Comment | Thermal Transitions |
|---|---|---|
| EMIBTI | Standard | −17 C. |
| EMIBTI/TEABTI | 70/30 Mix Some solid | −2.5 C. |
| EMIBTI/EMIBF4 | 50/50 Mix Some solid | None |

-continued

| Formula | Comment | Thermal Transitions |
|---|---|---|
| EMIBTI/EMIPF6 | 50/50 Mix | None |
| EMIBTI/TEABF4 | 80/20 Mix Near solid | −20 C. (Tm) |
| EMIBTI/TBAP | 90/10 Mix Some solid | −11 C. |
| EMIMS | Viscous Liquid | 15 C. (Tm) |
| PolyetherIBTI | Viscous Liquid | None |

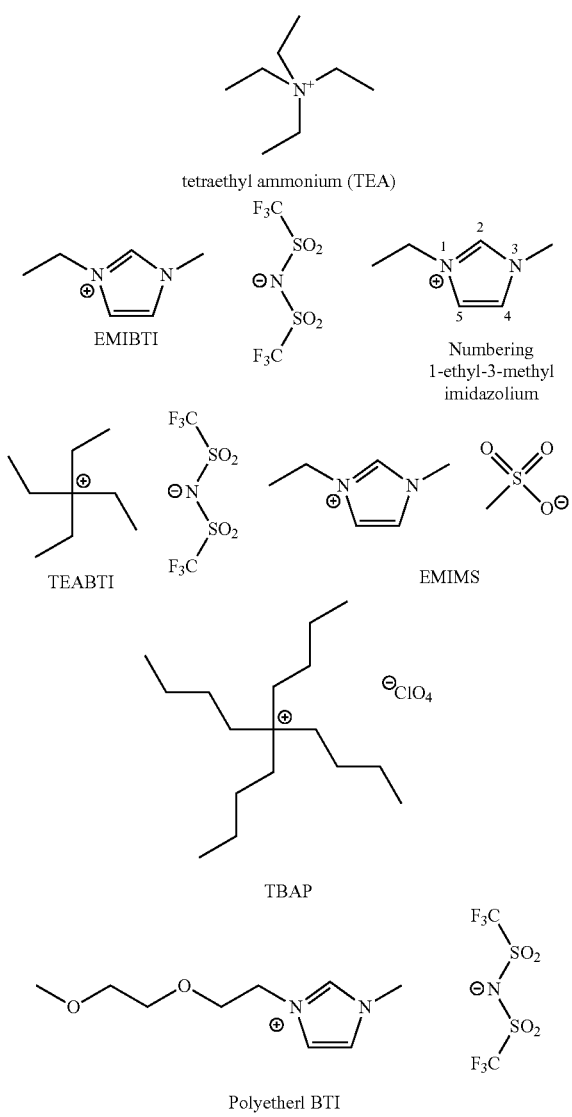

EXPERIMENTAL

EMIBTI was synthesized, purified, and analyzed according to procedures published previously. (J. D. Stenger-Smith, C. K. Webber, N. A. Anderson, A. P. Chafin, K. Zong, and J. R. Reynolds, *J. Electrochem. Soc.*, 149, A973 (2002)). 1-Ethyl-3-methylimidazolium hexafluorophosphate (EMIPF6) was obtained from Aldrich, and then recrystallized from ethanol three times and dried under vacuum for 8 h. All reagents were stored in an MBraun Unilab glove box with a dry nitrogen atmosphere. The synthesis of poly(propylene-dioxy-thiophene) (PProDOT) was performed using a procedure similar to that published by Welsh et al. (D. Welsh, A. Kumar, E. W. Meijer, and J. R. Reynolds, *Adv. Mater.*, 11, 1379 (1999)). PProDOT was recrystallized from ethanol and stored in a glove box.

Electrochemical growth of PProDOT and testing of PPro-DOT supercapacitors: All electrochemistry was performed using a Pine bipotentiostat. ProDOT was electrochemically grown according to our published procedure onto 5.0 mm diameter gold electrodes from Pine Research Instrumentation using EMIBTI as the supporting electrolyte in a glove box. (J. D. Stenger-Smith, C. K. Webber, N. A. Anderson, A. P. Chafin, K. Zong, and J. R. Reynolds, *J. Electrochem. Soc.*, 149, A973 (2002); J. D. Stenger-Smith, J. A. Irvin, D. J. Irvin, T. Steckler, and J. R. Reynolds, *Polym. Mater. Sci. Eng.*, 99, 699 (2008)). The films were stored in either the neutral or oxidized state depending upon their use as a cathode or anode. A Cincinnati Sub-Zero (CSZ) model 303 environmental chamber was used to test device performance between −60 and +60° C.

Physical property analysis of binary mixtures: The goal of this analysis was to check for crystallization or other physical instabilities that could limit the operability of devices at temperatures as low as −60° C. Although the creation of a complete phase diagram with well-determined crystal structures for the entire binary system would be ideal, doing so was judged beyond the scope of warranted effort. Therefore, a simple approach was adopted using differential scanning calorimetry (DSC) with appropriate thermal histories to check for any evidence of crystallization or cocrystallization, and cloud point measurements to check for any evidence of phase separation. These measurements were performed on the pure EMIBTI, pure EMIPF6, and the 50/50 by weight mixture of the two. The mixtures were prepared by weighing out approximately 0.05 g of each component into a glass vial, which was then tightly sealed with a Teflon-lined cap. To ensure homogenization, the 50/50 mixture was heated at 80° C. for 10 min; the 100% EMIBTI and 100% EMIPF6 were heated at 200° C. for 10 min. This was followed by a quench consisting of placing the vial in a jet of compressed nitrogen for 1 min and then immersion in water at approximately 10° C. for 1 min. The storage conditions for any samples not immediately tested after quenching were tracked and noted.

The DSC experiments were carried out using a TA Instruments Q100 scanning calorimeter under a nitrogen flow of 50 mL/min. For heating, a ramp rate of 10° C./min was used, while for cooling, a slow ramp rate of 1° C./min was utilized to afford ample time for crystallization (all of the slow cool DSC samples were immediately tested). Annealing temperatures of −20, −40, and −60° C. for up to 1 h were used. For each run, the sample was equilibrated at +60° C., followed by a slow cooling to the annealing temperature, isothermal annealing (which was skipped in some runs), and lastly, heating to +60° C. The cloud point measurements were carried out using a visual inspection of the small vials of the samples cooled in 5° C. increments at approximately 1° C./min, with approximately 15 min provided for equilibration at each temperature, down to −60° C. in the environmental chamber. The viscosity of the pure EMBTI and the mixture were measured at room temperature using the falling sphere method (average of a minimum of three runs).

Scanning electron microscopy: PProDOT polymer films were grown according to previous method described in J. D. Stenger-Smith, C. K. Webber, N. A. Anderson, A. P. Chafin, K. Zong, and J. R. Reynolds, *J. Electrochem. Soc.*, 149, A973 (2002)) which is hereby incorporated by reference. Cylindrical platinum electrodes (1.6 mm diameter BASi model MF-2013) were used to deposit the PProDOT films. EMIBTI and EMIBTI/EMIPF6 mixtures were used as supporting electrolytes. Identical deposition conditions were used (100 mV/s, −0.800 to +1.70 V window, 24 full cycles) for both electrolyte systems. Films were blotted dry with a thin paper wipe and dried under vacuum for 6 hrs. Due to the conductive nature of the films, a gold coating was not necessary. Electron microscopy of the electrode ends employed a Zeiss EVO-50 scanning electron microscope (SEM). Most images were taken using 20 kV accelerating voltage and a calculated beam current of 10-25 pA. Images were collected using either a secondary electron (SE) or a quadrapole backscatter detector (QBSD). The SE detector is the normal imaging detector (it shows surface topography) and the QBSD shows gray scale differences based on average atomic weight (the higher the atomic weight, the brighter the image area). Working distance was approximately 9 mm. Locations on the electrode ends before and after coating were imaged. After coating, areas of thin coating as well as areas of thick coating were examined.

Construction of capacitors: PProDOT was electrochemically deposited using a method similar used in previous work described in reference J. D. Stenger-Smith, C. K. Webber, N. A. Anderson, A. P. Chafin, K. Zong, and J. R. Reynolds, *J. Electrochem. Soc.*, 149, A973 (2002) which is hereby incorporated by reference. Instead of the cylindrical electrodes described above, flexible gold-coated Kapton electrode substrates were used. Electrode substrates were prepared using 2 mil DuPont Kapton HN. A shadow mask was applied before the sputter deposition of a chromium adhesion promoting layer (50-100 Å), followed by the sputter deposition of gold (2000 Å). Device fabrication was then conducted entirely within a glove box under nitrogen. Polymer films were electrochemically deposited onto the substrates, leaving ca. 1 cm of the substrate uncoated by polymer. Next, a piece of 20 μm thick battery separator paper was placed between the two electrodes. The electrodes were encapsulated using a 25 μm ShieldPack Polymer Products Department (PPD) barrier material, leaving ca. 1 cm of each electrode substrate extending beyond the barrier material for electrical contact. The device was then heat sealed along two sides, and one end using an impulse heat sealer. Electrolyte was added (ca. 1 mL), and excess nitrogen and electrolyte were forced out of the open end of the device before the heat sealing of the fourth side. The sealed device was then removed from the glove box for testing. All testing was done in a CSZ MCH model 303 environmental chamber atmosphere using two-electrode cyclic voltammetry (reference and working electrodes shorted together). The capacitors were equilibrated for 10 s at 0 V before electrochemical cycling. FIG. 1 is of hermetically sealed two-electrode supercapacitor construction.

Figure 2A:
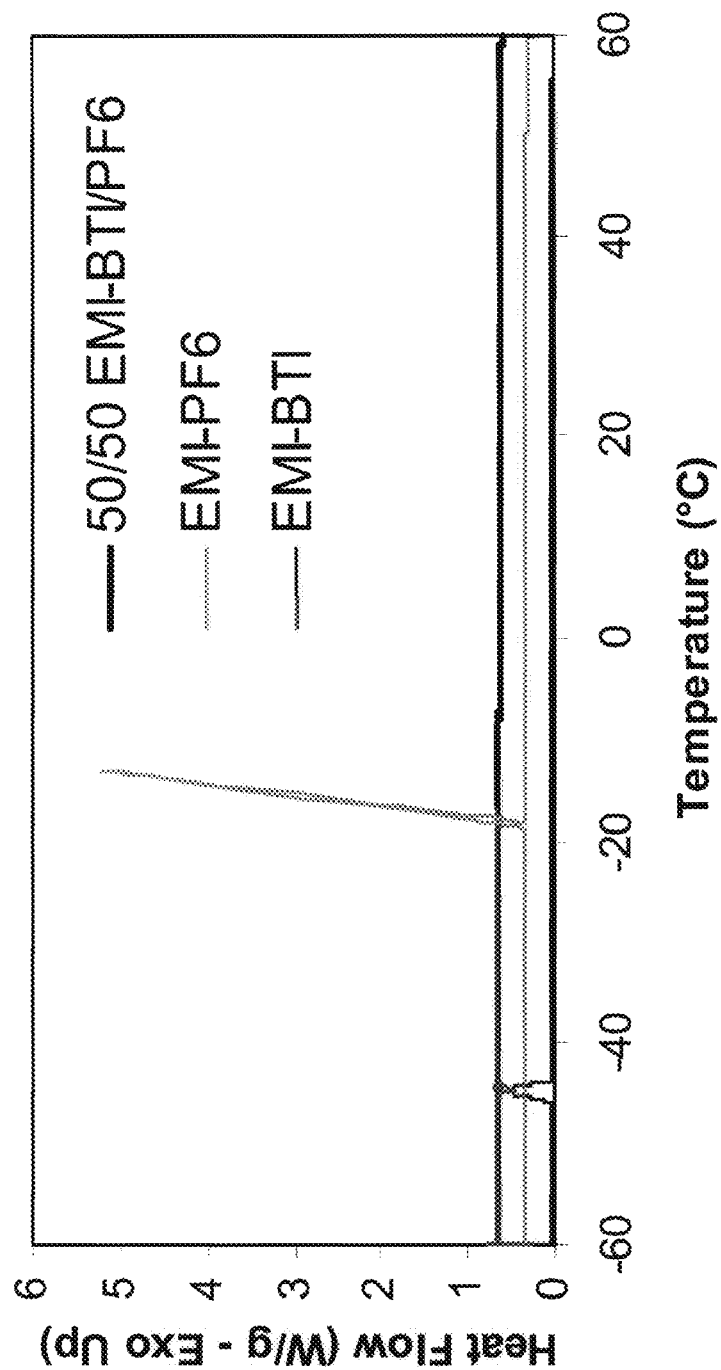
FIGS. 2a and 2b are graphs showing DSC traces of pure EMIBTI, pure EMIPF6, and a 50/50 by weight mixture of the two on (a) cooling at 1° C./min (b) subsequent heating at 10° C./min. The curves are progressively offset by 0.3 W/g for clarity, according to embodiments of the invention.
Figure 2B:
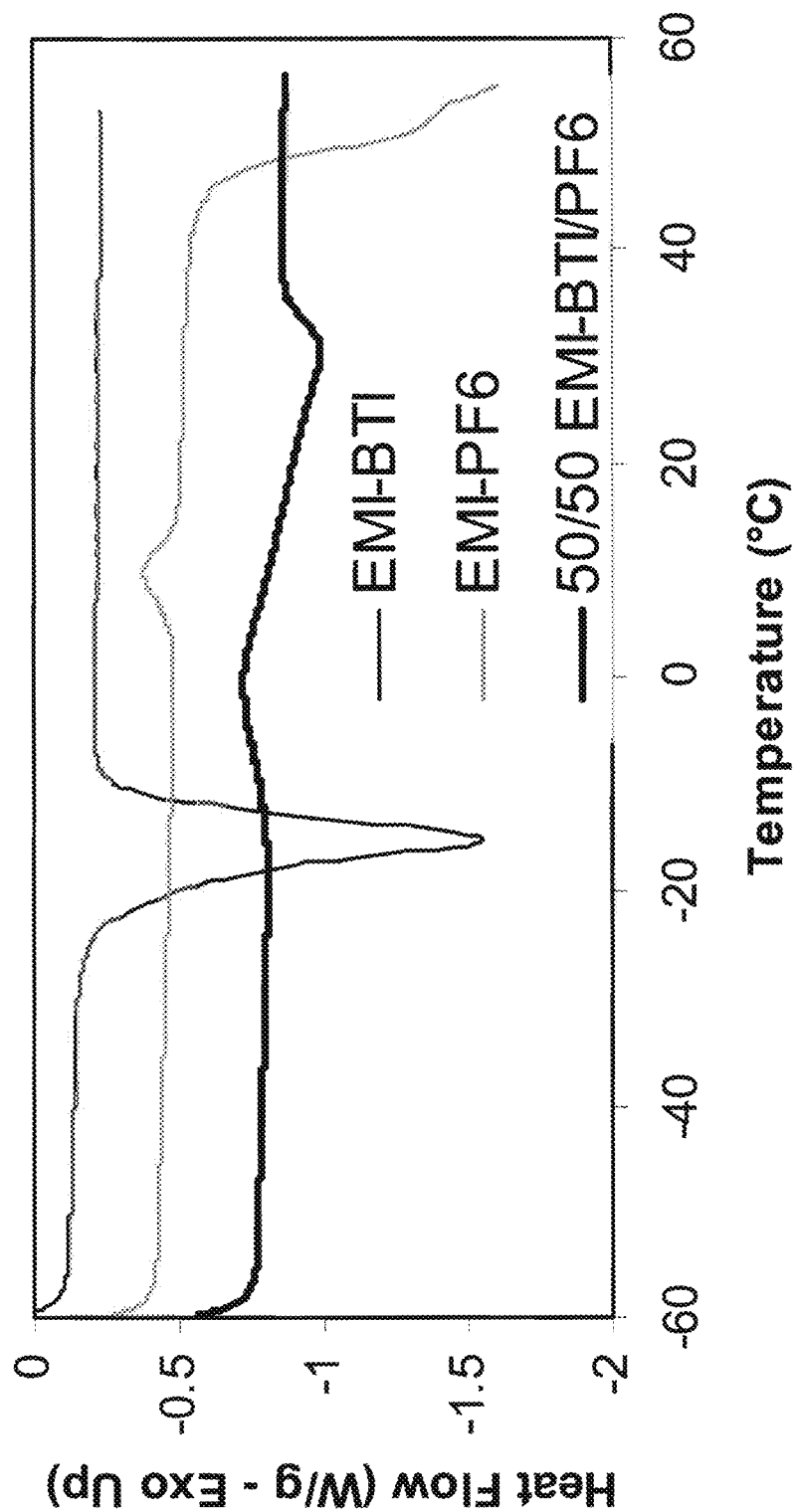

Results: Physical properties: FIGS. 2a and 2b compares the DSC traces of pure EMIBTI, pure EMIPF6, and the 5050 mixture of the two during slow cooling to −60° C. and the subsequent heating to +60° C.). DSC traces of pure EMIBTI, pure EMIPF6, and a 50/50 by weight mixture of the two on (a) cooling at 1° C. per minute; and b) subsequent heating at 10° C. per minute. Note that the curves are progressively offset by 0.3 W/g for clarity. Both pure EMIBTI and pure EMIPF6 crystallized rapidly on reaching a consistent degree of supercooling, whereas no crystallization of the 50/50 mixture was observed. The very rapid crystallization of pure EMIPF6 (complete in less than 1 min) generated enough heat to temporarily overwhelm the DSC temperature control system, resulting in the tilted peak shape shown in FIG. 2a. The increased rate of crystallization in EMIPF6 is most likely due to the larger degree of supercooling. The heat of crystallization was measured at 37 J/g for EMIBTI and at 50 J/g for EMIPF6 during cooling, but due to the high rate of crystallization, these measurements are subject to substantial error.

Slow crystal growth was never observed for the pure compounds. When held at −40° C. for an hour, for instance, pure EMIBTI exhibited no crystallization for approximately 45 min, then rapidly crystallized in under 5 min, presumably due to a triggering nucleation event. When held at −20° C., no crystallization of pure EMIBTI was ever observed. No crystallization was ever observed for the 50/50 mixture on holding for up to 1 h, at temperatures as low as −85° C. Moreover, no cloud point was observed during cooling of the 50/50 mixture in the environmental test chamber (which represents a total annealing time of 135 min over the temperature range from −20 to −60° C.). Thus, significant crystallization during cooling was effectively suppressed by the use of the mixture, which showed no signs of phase separation.

Some crystallization of the EMIBTI/EMIPF6 mixture can be induced, however, as evidenced by FIGS. 2a and 2b. The pure EMIBTI melted reproducibly at an onset temperature of −20° C., with a distinct peak at −15° C. and a heat of melting of 48±2 J/g. The pure EMIPF6 showed some signs of residual crystal growth over the range 5-15° C., followed by an onset of melting at about 40° C. The difference in the behavior of the EMIBTI and EMIPF6 was most likely a result of the different crystallization rates; the fast-growing crystals of EMIPF6 were likely more disordered and therefore able to reorganize when heated close to the melting temperature.

The 50/50 mixture also showed signs of crystal growth over a broader temperature range (from −15 to +15° C.), but with a heat of melting of only around 10 J/g, with around 9.5 J/g accounted for by the observed growth on heating, and a melting onset around 15° C. Quantitatively similar behavior was seen when the mixture was cooled to −85° C. instead of −60° C., and when the mixture was held at −60° C. for an hour before heating. The intermediate melting point and broad melting range seen in the mixture are suggestive of cocrystallization with a somewhat variable composition, but much more data would be required to draw a definitive conclusion. One explanation for the observed crystallization and melting during heating but not cooling would be that small, slow-growing nuclei formed at a temperature between the observed nucleation thresholds of the two pure components (from −40 to −20° C.), and that these were able to grow gradually when heated to near the melting point.

Therefore, although it may not depress the melting point sufficiently to prevent crystallization entirely, the use of the mixed ionic liquid system, nonetheless, greatly hinders crystallization at temperatures as low as −60° C. Moreover, unlike with the pure compounds, when crystals do grow, they tend to grow gradually rather than in one rapid burst. Thus, even when a thermal history that promoted crystal growth was encountered in an operating supercapacitor, the result would likely be a slow and partial loss of performance rather than a complete shutdown. Lastly, because EMIBTI and EMIPF6 do exhibit somewhat different crystallization tendencies, there is a good chance that a mixture with a composition other than 50/50 by weight could suppress crystallization even more effectively. The viscosity of the pure EMIBTI and the 50/50 EMIBTI/EMIPF6 mixture was 28±1 and 29±1 cP, respectively.

EMIBTI supported supercapacitor: PProDOT was electrochemically deposited as described above. Several attempts were made to deposit PProDOT from the EMIBTI/EMIPF6 mixture, along with a study in which the composition of the EMIBTI/EMIPF6 was varied from 50/50 to 95/5. In all cases including the EMIBTI/EMIPF6 mixture, the electrochemical activity of these films was poor.

It was suggested that there may be some residual water in the EMIPF6 which may disrupt electrodeposition. An elemental analysis was performed on the EMIPF6: Calculated/found: C, 28.13/27.96, H, 4.32/4.31, N, 10.94/10.74, and F: 44.50/44.21. Chloride was not detected (below 0.01%) and oxygen/water analysis could not be performed on high fluorine samples. (Atlantic Microlabs, Memorandum (August 2009)). However, with the very close agreement of the elemental analysis with the calculated value (especially given the high concentration of fluorine in the sample), and the ratio of hydrogen to carbon (which would be higher because water is 11.1% hydrogen by mass), and no evidence of water loss during thermal analysis, it is highly unlikely that there is any significant amount of water present in EMIPF6.

The cyclic voltammograms of the attempts at film growth from the EMIBTI/EMIPF6 mixture did not resemble those of PProDOT grown using EMIBTI. Devices constructed using these particular films (which did not resemble films of PProDOT), showed very poor capacity (less than 30% of the capacity of the EMIBTI supported devices in the absolute best of cases, and behaved more like resistors at higher scan rates. The charge capacity of these devices also degraded significantly (down to less than 15% of the initial capacity) after fewer than 100 cycles.

Films grown from the EMIBTI/EMIPF6 mixture were compared to the films grown from EMIBTI using an SEM. The overall micrographs clearly indicated the disparity in polymer deposition between the EMIBTI supported growth and the EMIBTI/EMIPF6 supported growth with inferior growth evident from the EMIBTI/EMIPF6 mixture (Reference Stenger-Smith et. al; 21 Jan. 2010, Journal of The Electrochemical Society (Vol. 157, No. 3). Elemental analysis using a quantum backscatter of the respective films is summarized in

TABLE I

Summary of elemental analyses of films grown from pure EMIBTI and from EMIBTI/EMIPF6 mixture.

| Element | EMIBTI (atom %) | EMIBTI/PF6 mix (atom %) |
|---|---|---|
| Overall | | |
| Carbon | 52.67 | 54.83 |
| Nitrogen | 8.81 | 8.97 |
| Fluorine | 11.81 | 11.93 |
| Phosphorous | 0.78 | 1.52 |
| Sulfur | 7.19 | 4.55 |
| Oxygen | 14.36 | 12.33 |
| Chlorine | — | 0.31 |
| Pt (electrode) | 4.28 | 5.54 |
| Thick section | | |
| Carbon | 58.01 | 62.26 |
| Nitrogen | 8.06 | 6.85 |
| Fluorine | 10.47 | 8.40 |
| Phosphorous | 0.49 | 1.44 |
| Sulfur | 7.79 | 6.55 |
| Oxygen | 12.41 | 10.25 |
| Chlorine | — | — |
| Pt (electrode) | 2.77 | 5.54 |
| Thin section | | |
| Carbon | 62.27 | 57.73 |
| Nitrogen | 10.71 | 8.89 |
| Fluorine | 3.85 | 5.33 |
| Phosphorus | 1.52 | 2.39 |

TABLE I-continued

Summary of elemental analyses of films grown from pure EMIBTI and from EMIBTI/EMIPF6 mixture.

| Element | EMIBTI (atom %) | EMIBTI/PF6 mix (atom %) |
|---|---|---|
| Sulfur | 4.06 | 6.55 |
| Oxygen | 8.72 | 6.82 |
| Chlorine | — | 0.15 |
| Pt (electrode) | 8.87 | 14.52 |

The quantum backscatter elemental analysis reveals some interesting observations. There is very little phosphorus incorporated into the EMIBTI/EMIPF6 films, although quantitative analysis is difficult due to the proximity of the Pt peak and the thinness of the EMIBTI/EMIPF6 film. A small amount of chloride is detected in the EMIBTI/EMIPF6 films (though this is close to the detection limit). The atomic percentages of carbon, hydrogen, fluorine, oxygen, and nitrogen are, within limits, nearly identical for both films.

Based upon these results, the lack of polymer growth is most likely due to the generally accepted fact that some monomers grow and switch rather poorly in certain electrolytes. P. Evans, in *Advances in Electrochemical Science and Engineering*, H. Gerischer and C. W. Tobias, Editors, Vol. 1, pp. 1-74, VCH, Weinheim (1990). Low levels of phosphorus incorporation in the film may indicate that PF6 anions are excluded from the polymer during growth and switching. It is also possible that trace amounts of impurities in EMIPF6 (undetectable using elemental analysis) may inhibit polymerization. B. R. Clare, P. M. Bayley, A. S. Best, M. Forsyth, and D. R. MacFarlane, *Chem. Commun.* (Cambridge), 2008, 2689; J. Zhang and A. M. Bond, *Analyst* (Cambridge, UK.), 130, 1132 (2005); P. Nockemann, K. Binnemans, and K. Driesen, *Chem. Phys. Lett.*, 415, 131 (2005); J. H. Davis, Jr., C. M. Gordon, C. Hilgers, and P. Wasserscheid, *Ionic Liquids in Synthesis*, pp. 7-21, Wiley-VCH Verlag, Weinheim (2003); K. R. Seddon, A. Stark, and M.-J. Tones, *Pure Appl. Chem.*, 72, 2275 (2000).

To achieve superior polymer growth, PProDOT was electrochemically deposited using EMIBTI as the supporting electrolyte rather than the EMIBTI/EMIPF6 mixture. EMIBTI/EMIPF6 was then used as the supporting electrolyte during polymer switching to improve low temperature performance. The configuration used in previous work was described in J. D. Stenger-Smith, C. K. Webber, N. A. Anderson, A. P. Chafin, K. Zong, and J. R. Reynolds, *J. Electrochem. Soc.*, 149, A973 (2002) and did not lend itself well to cycling in the temperature chamber. In particular, there was a significant amount of electrolyte leakage observed during the cycling process followed by significant degradation of device performance. Even after the lost electrolyte was replaced, the devices recovered only about 60% of their original capacity.

To prevent electrolyte leakage as well as to prevent reactions with air, devices were hermetically sealed. Sealed and unsealed supercapacitors were constructed and subject to identical temperature histories. The unsealed supercapacitor showed evidence of significant leakage after heating to 60° C. (about 65% of the initial electrolyte mass), followed by loss of over 90% capacity. The hermetically sealed capacitor shows essentially no loss of capacity. The sealed capacitor has identical capacity both before and after heating. The original unsealed capacitor shows significant leakage/loss after heating to 60° C. The degradation of the unsealed capacitor is most likely due to mechanical disruption of the film due to lack of electrolyte.

Figure 3:
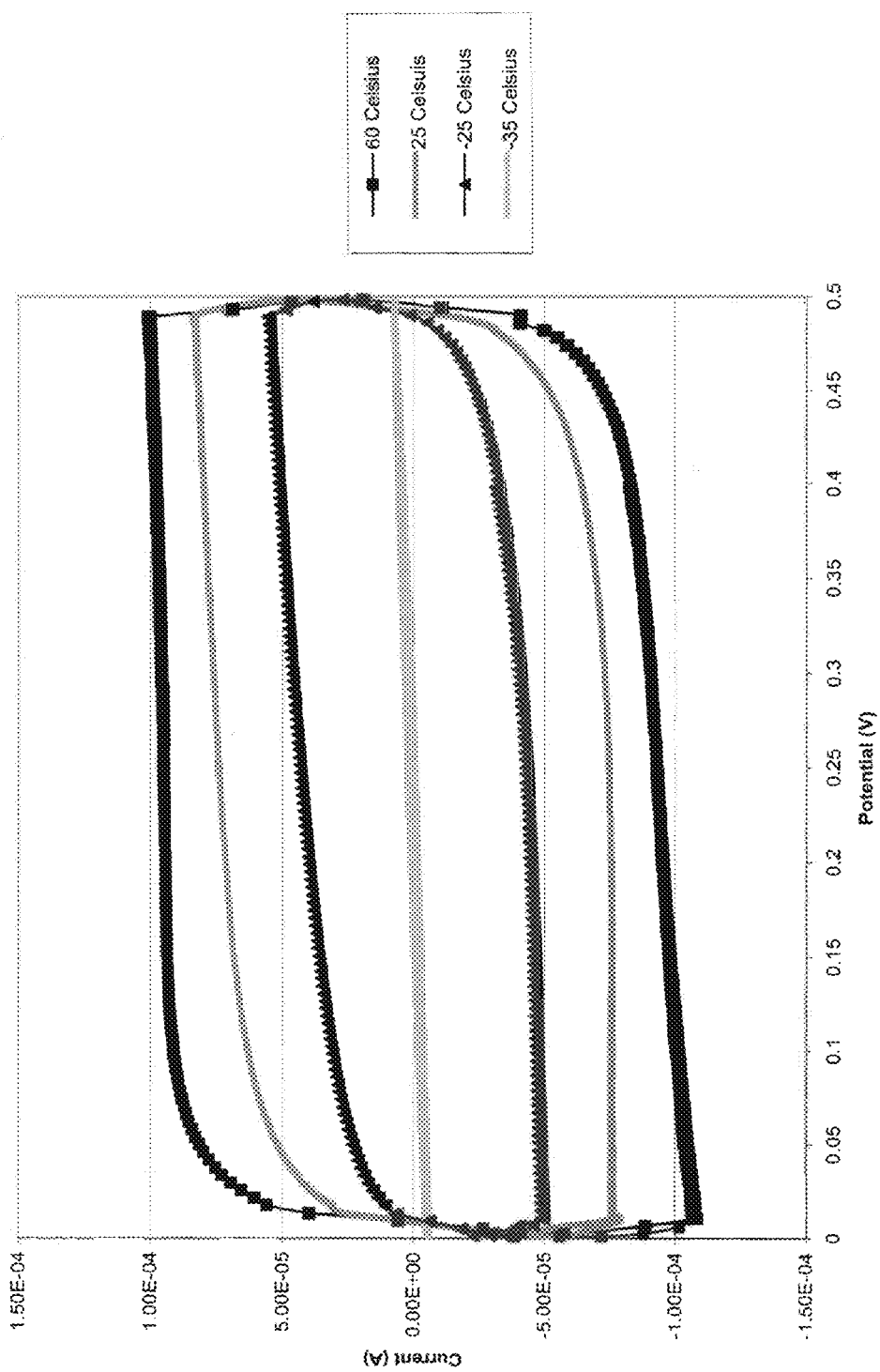
FIG. 3 is a graph showing a study of temperature dependence of the behavior of the EMIBTI cell, according to embodiments of the invention.

FIG. 3 shows the temperature behavior of the supercapacitor using EMIBTI as the supporting electrolyte at a scan rate of 500 mV/s. The device maintains its capacitive behavior down to approximately −25° C. (confirmed by repeated experiments), which is below the melting point of EMIBTI (−17° C.). At −35° C. the device behaves as a classic resistor.

Figure 4:
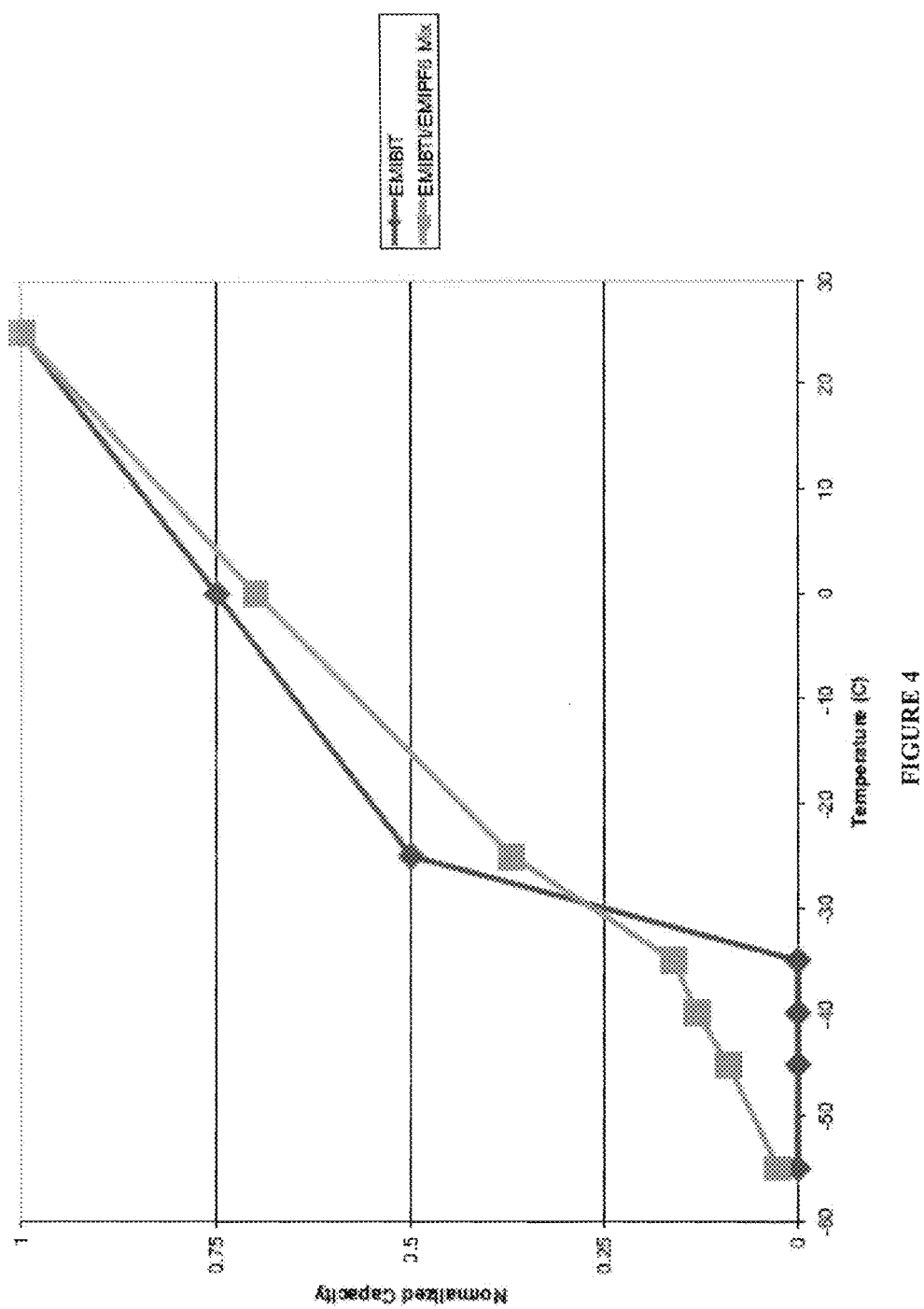
FIG. 4 is a graph showing a comparison of capacity vs temperature for EMIBTI cell (dark) and EMIBTI/EMIPF6 cell (light), according to embodiments of the invention.

FIG. 4 compares the capacity retention behavior of EMIBTI and EMIBTI/EMIPF6-based devices as a function of temperature. Although the EMIBTI/EMIPF6-based devices have slightly less capacity retention at −25° C. than the EMIBTI-based devices (due most likely to EMIBTI/EMIPF6 having a higher viscosity), the EMIBTI/EMIPF6-based devices retain capacitive behavior down to −60° C. (although the capacity of the EMIBTI/EMIPF6 device at −60° C. was only 2.6% of the room-temperature capacity).

Figure 5:
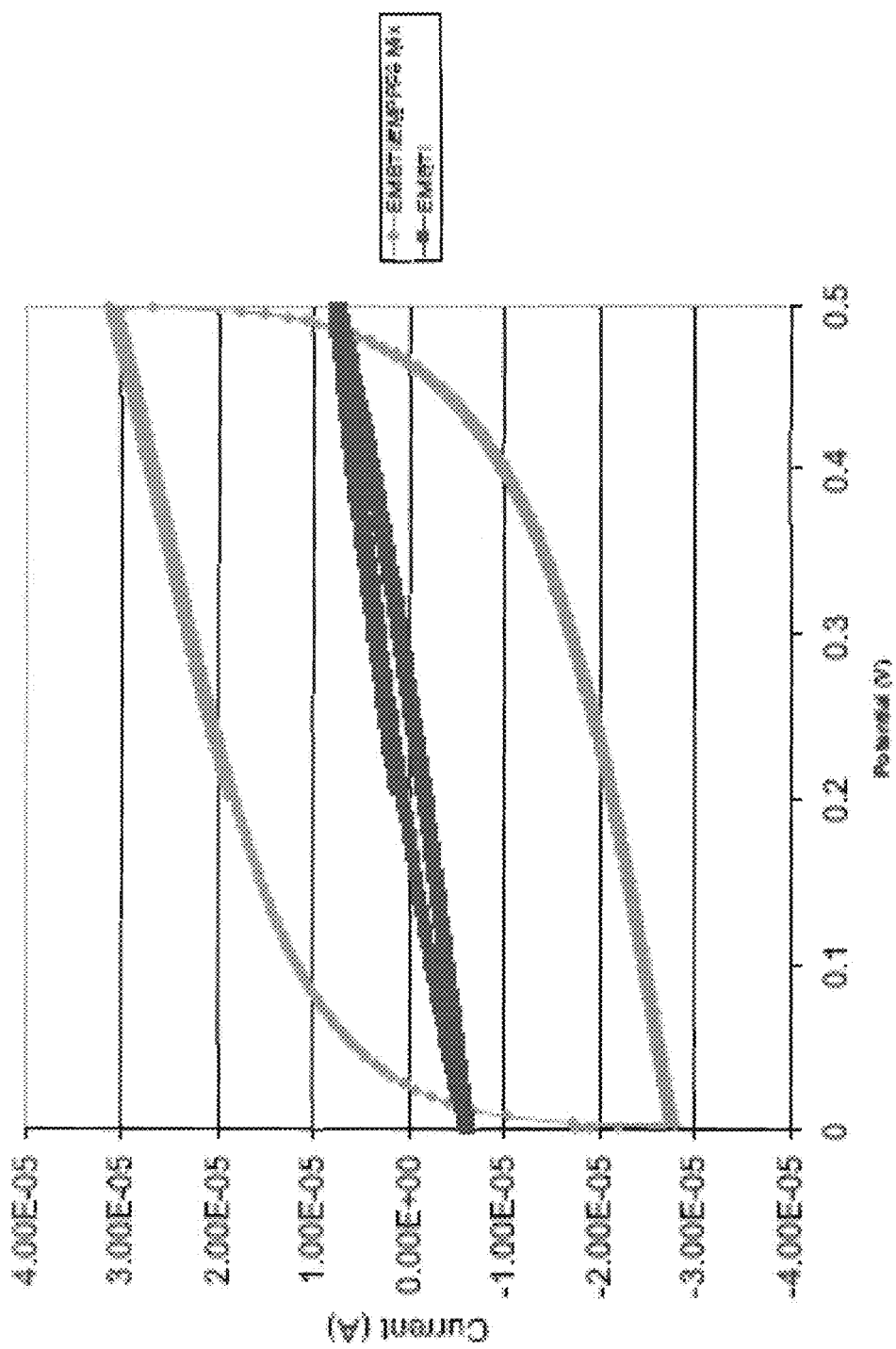
FIG. 5 is a graph showing a demonstration of capacitive behavior of EMIBTI/EMIPF6 cell (light) and resistive behavior of EMIBTI cell (dark) at −35° C., according to embodiments of the invention.
Figure 6:
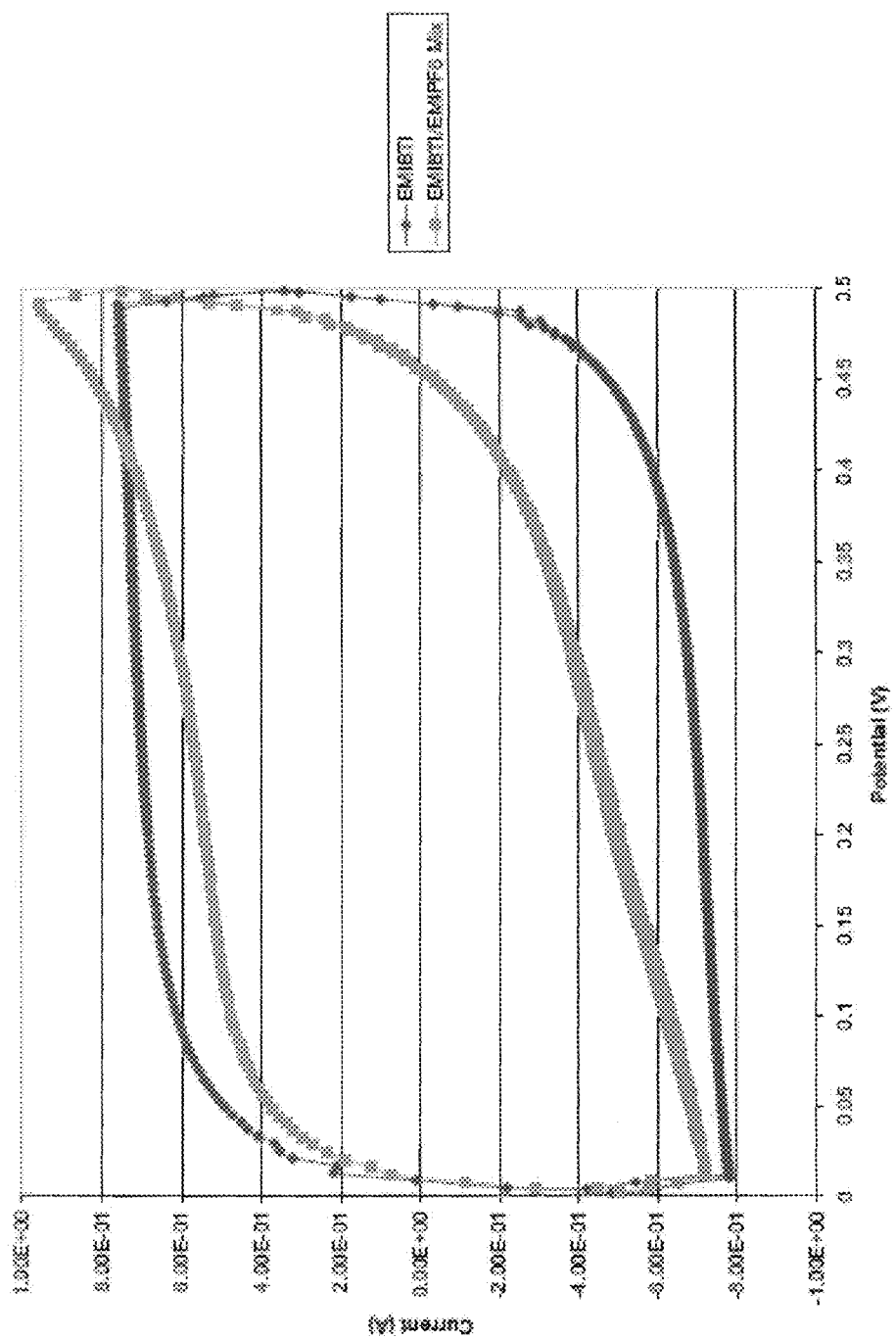
FIG. 6 is a graph showing a comparison of charge-discharge behavior of EMIBTI cell (dark) and EMIBTI/EMIPF6 cell (light) at 60° C. and 100 mV/s, according to embodiments of the invention.

FIG. 5 shows the comparison of the EMIBTI/EMIPF6-based device to the EMIBTI-based device at −35° C., illustrating the difference in behavior of EMIBTI/EMIPF6 (capacitive) and EMIBTI (resistive). The charge-discharge behavior was examined for both the EMIBTI and EMIBTI/EMIPF6-based supercapacitors at 60° C. at 100 mV/s. Both devices show classical capacitive behavior, with fast response to sweep direction changes. The performance of the device with the EMIBTI as the supporting electrolyte was slightly better than that of the EMIBTI/EMIPF6-based supercapacitor. The coulombic efficiency of both devices (ratio of cathodic to anodic current–the ratio of charge for the oxidative and reductive currents) is >98% for both devices; indicating reversible charge transfer.

Long-term and high temperature cycling of EMIBTI/EMIPF6-based devices show good performance with reasonable stability. The EMIBTI/EMIPF6-based devices lose approximately 10% capacity after 150 cycles at 60° C., then appear to level off and maintain this capacity up to 10,000 cycles at 70% depth of discharge. The EMIBTI-based devices do not lose any measurable capacity; devices lose less than 1% capacity over several tens of thousands of cycles, within error detection limits.

Conclusions of Research: An ionic liquid mixture was formulated and compared to EMIBTI. Based upon the thermal analysis, rapid crystallization of 50/50 wt % mixture of EMIBTI with EMIPF6 at or above −50° C. can be completely ruled out. A hermetic sealing protocol was developed and demonstrated to help devices retain electrolyte, prevent reactions with air, and preserve capacity. This mixture did not support the growth of electroactive PProDOT on gold/platinum electrodes, which was confirmed by multiple analyses of the charge capacity of the devices made with the mixture and detailed scanning electron measurements that compared the films made from the mixture with those made from EMIBTI. However, this mixture does support the operation of a supercapacitor (comprising PProDOT films deposited from an EMIBTI-based electrolyte) at temperatures below −35° C. The charge, energy, and power storage as well as the reversibility of EMIBTI/EMIPF6-based supercapacitors at higher temperatures were nearly as good as the performance of supercapacitors using pure EMIBTI.

Electroactive Polymer Based Electrochemical Supercapacitors Using Poly(benzimidazo-benzophenanthroline), (BBL) and its Pyridine derivative Poly(4-aza-benzimidazo-benzophenanthroline), (Pyr-BBL) as Cathode Materials.

Another aspect of the invention includes a process used to solution cast films of BBL and Pyr-BBL, which were used as cathode materials in Type IV supercapacitors. This processing technique involves co-casting the polymer from solution with a room temperature ionic liquid, EMIBTI. The new processing technique gave polymer films with superior transport properties; there was no break-in period for the co-cast films and the co-cast films also had higher charge capacity than the standard films. Co-cast films of BBL and Pyr-BBL were incorporated into Type IV supercapacitors using PProDOT as the anode material. It was found that the PProDOT-BBL supercapacitors store about 50% more average energy than a comparable PProDOT-Pyr-BBL supercapacitor, although the difference in average power delivered by the two devices is small due to the better frequency response of the PProDOT-Pyr-BBL supercapacitor. The PProDOT-Pyr-BBL devices were found to be far more stable than PProDOT-BBL devices, lasting at least five times as long.

Conjugated polymers have a wide range of uses due to the property changes of the materials in their different states of oxidation. From neutral light-harvesting semiconductors to doped transparent electrode materials, the uses are as wide and varied as the number of polymer systems studied. One of the areas of importance to the Navy is charge storage, not only as battery materials, but also the in thin film supercapacitors. Traditional reasons for using polymer-based systems include the potential for lighter weight, lower cost, more damage resistant, and less rigorous and more flexible packaging. Electroactive polymer-based supercapacitors also offer the potential for increased charge storage capacity, because the entire volume of the polymer should be available for charge storage, whereas in traditional inorganic metal oxides, only the surfaces of the particles participate in the charge storage process. (Stenger-Smith, J. D.; Webber, C. K.; Anderson, N.; Chafin, A. P.; Zong, K. K.; Reynolds, J. R., *J. Electrochem. Soc.* 2002, 149, A973)

Supercapacitor (NEC) and Ultracapacitor (Pinnacle) were trademarks of early electrochemical capacitor companies in the 1970s. (Irvin, J. A.; Irvin, D. J.; Stenger-Smith, J. D., Electrically Active Polymers for Use in Batteries and Supercapacitors. In *Handbook of Conducting Polymers*, Skotheim, T.; Reynolds, J. R., Eds. Taylor and Francis: Boca Raton, 2007) These terms have since been broadened to describe any double layer or redox capacitor with specific energy and specific power intermediate to batteries and electrostatic capacitors respectively. Typically, an ultracapacitor is a device comprised of two carbonaceous electrodes, and a supercapacitor is a similar device in which two carbonaceous electrodes are catalyzed with metal oxides such as $RuO_2$. The use of electroactive polymers as the electrode materials in supercapacitors was popularized by Rudge et. al, in 1994. (Arbizzani, C.; Mastragostino, M.; Meneghello, L., *Electrochim. Acta* 1996, 41, 21) While there are many earlier papers that fall under the guidelines set forth by Rudge et al, the devices were described as batteries by the authors. Since then, a wide range of materials and architectures have been explored in electroactive polymer based supercapacitors.

Poly(benzimidazobenzophenanthroline) (BBL) was first made as a temperature resistant insulating polymer. The material is difficult to process due to its poor solubility. Jenekhe later found that BBL can be dissolved at higher concentrations in nitromethane with lewis acids such as aluminum and gallium chloride, with solution concentration as high as 20 weight percent allowed for more facile processing of thin films. (F. E. Arnold, R. L. Van Deusen, *Macromolecules* 1969, 2, 497-502)

One of the first electrochemical analysis done on BBL was in aqueous acid. (K. Wilbourn, R. W. Murray, *Macromolecules* 1988, 21, 89-96; b.) X. L. Chen, S. A. Jenekhe, *Macromolecules* 1997, 30, 1728-1733; c.) A. Babel, S. A. Jenekhe, J. Am. Chem. Soc. 2003, 125, 13656-13657; M. M. Alam, S. A. Jenekhe, *Chem. Mater.* 2004, 16, 4647-4656) Since the electron affinity of BBL is around 4.4 eV reductive electrochemical doping is performed at a higher potential than most electroactive polymers.

Another aspect of the invention is a method for processing of the cathode material poly(benzimidazole benzophenanthroline) (BBL) and Poly(4-aza-benzimidazobenzo-phenanthroline), (Pyr-BBL) and the electrochemical properties of these materials. In addition, there is an analysis and comparison of thin film electroactive polymer based Type IV supercapacitors with a working voltages of >2.0 volts using BBL and Pyr-BBL as the cathode material.

Experimental Results

Ionic Liquids: EMIBTI (1-ethyl-3-methylimidazolium bis(trifluoromethylsulfonyl)-imide) was synthesized from lithium bis(trifluoromethylsulfonyl)imide and 1-ethyl-3-methylimidazolium chloride and purified via column chromatography. All other chemicals were purchased from Aldrich and used as received.

Films for SEM Analysis: The as-received BBL was dissolved at 1 wt % in methanesulfonic acid (MSA) at 80-100° C. over 24-72 hours. Additional samples of BBL in MSA were prepared having EMIBTI (i.e. 35% BBL and 65% EMIBTI). Solutions were drop cast onto glass slides or gold coated glass slides at 140° C. in air and heated for ~2 hrs. The resulting brassy films were dried in a vacuum oven at 100° C. for at least 24 hrs under dynamic vacuum. Film samples co-cast with IL were rinsed with methanol or methylene chloride to remove residual IL. The BBL samples for scanning electron microscopy were sputter coated with iridium and scanned in a similar processing was performed for Pyr-BBL films.

Reagents: 2,3,5,6-Tetramino pyridine trihydrogen chloride monohydrate was obtained by the reduction of 2,6-diamino-3,5-dinitro pyridine with $Sn^0$ and aqueous HCl. (Sikkema, D. J. Nitration of Pyridine-2,6-diamines. 5945537, 1999) Naphthalene dianhydride (Aldrich) was sublimed twice prior to use. Polyphosphoric acid and poly(benzimidazobenzophenanthroline) (BBL) were used as received (Aldrich).

New BBL Synthetic Process: The heretofore synthesis of poly(benzimidazobenzophenanthroline) (BBL) has relied on a co monomer that is very sensitive towards oxidation, 1,2,4,5-tetraminobenzene (TAB) and its slightly more stable tetrahydrochloride salt (TAB.4HCl). (F. E. Arnold, R. L. Van Deusen, *Macromolecules* 1969, 2, 497-502) While this conventional method has been used with good results by various groups, it was determined to ensure as high a molecular weight as possible to ensure favorable properties in our end use, charge storage devices. To obtain the desired polymer properties, both comonomers, 1,4,5,8-naphthalenetetracarboxylic acid dianhydride (NTCA) and TAB, needed to be as pure and as stable as possible to guarantee the exact stoichiometry for the polycondensation reaction. In related work, 1,3-diamino-4,6-bis(p-toluenesulfonamido)benzene was synthesized to overcome the problems associated with TAB in the formation of high molecular weight polybenzimidazole. (R. F. Kovar, F. E. Arnold, *J. Poly. Sci.: Poly. Chem. Ed.* 1976, 14, 2807-2817)

Although it was found that 1,3-diamino-4,6-bis(p-toluenesulfonamido)benzene still oxidizes in the presence of oxygen and light over a period of hours, it is easily stable long enough to be weighed out and added to the reaction vessel in an open laboratory environment. This facilitated its use considerably, especially when compared to TAB, which oxidizes in a matter of seconds.

The polymerization process took into account a temperature and period of time to allow for the conversion of 1,3-diamino-4,6-bis(p-toluenesulfonamido)benzene to the free TAB (90° C., 6 h) and then the temperature is increased to the polymerization temperature for an extended period of time (180° C., 16 h).

Experimental: All chemicals were purchased from Aldrich and used as received, except for 1,4,5,8-naphthalenetetracarboxylic acid dianhydride, which was purchased from TCI, and sublimed before use. 1,3-(p-Toluenesulfonamido)benzene (1) was synthesized according to a modified procedure by reacting o-phenylenediamine with p-toluenesulfonyl chloride in the presence of pyridine in dichloromethane. (B. A. Lanman, A. G. Myers, *Org. Lett.* 2004, 6, 1045-1047) The comonomer was then synthesized with modifications to ease the purification of the final product. 1,3-Dinitro-4,6-(p-toluenesulfonamido)benzene (2) was formed by adding 1,3-(p-toluenesulfonamido)benzene to a solution of nitric acid in acetic anhydride. The nitro groups were then reduced via hydrogenation in degassed, anhydrous ethanol to yield 1,3-diamino-4,6-(p-toluenesulfonamido)benzene (3). An overview of the synthesis is shown in Scheme 1.

Scheme 1. Synthesis of 1,3-diamino-4,6-bis(p-toluenesulfonamido)benzene.

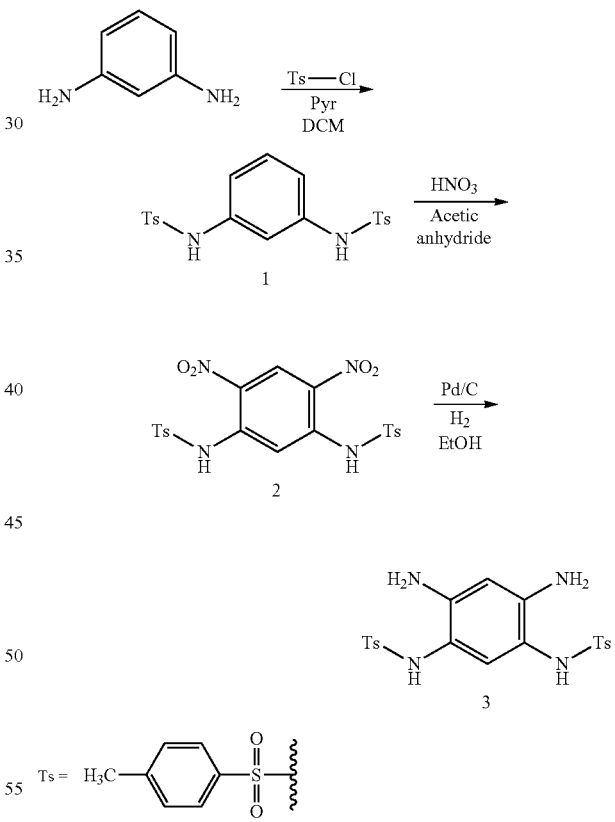

The copolymerization of NTCA and 3 occurred in polyphosphoric acid (PPA) and takes into account a temperature and period of time to allow for the conversion to the free TAB (90° C., 6 h) and then the temperature is increased to the polymerization temperature for an extended period of time (180° C., 16 h). After cooling the reaction mixture was precipitated in methanol. The residue was dissolved in methanesulfonic acid (MSA) and reprecipitated in methanol twice. The polymer synthesis is illustrated in Scheme 2 below.

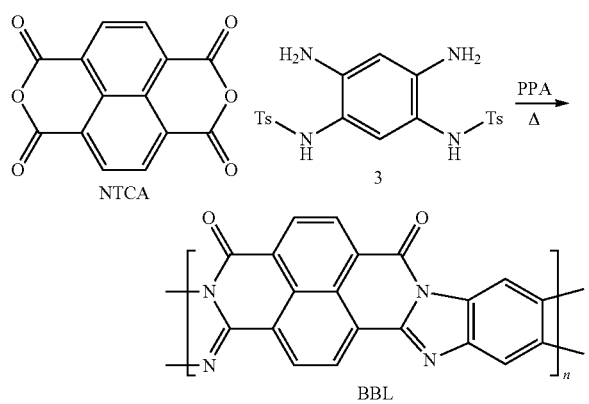

Scheme 2. Synthesis of poly(benzimidazolebenzophenanthroline) (BBL) or ladder-poly[(1,4,5,8-naphthalenetetracarboxylic acid)-alt-(1,2,4,5-tetraminobenzene)]. 1,3-(p-Toluenesulfonamido)benzene (1). Pyridine (56.1 mL; 694 mmol) was added to a solution of 1,3-phenylenediamine (15.0 g; 139 mmol) in anhydrous dichloromethane (500 mL) and cooled to 0° C. under nitrogen. p-Toluenesulfonyl chloride (63.5 g; 333 mmol) was added portion-wise to the reaction mixture and the temperature was allowed to warm to room temperature while stirring overnight. The reaction mixture was extracted with water, saturated aqueous sodium bicarbonate, and brine. The organic layer was dried over sodium sulfate, filtered, and concentrated in vacuo. Proton NMR showed only the product except for pyridine as a contaminant, so the residue was pumped under high vacuum over 48 h. Proton NMR showed that around one equivalent of pyridine was still present. Dissolved in ethyl acetate and extracted twice with 1 M aqueous hydrochloric acid, dried over sodium sulfate, filtered, and concentrated in vacuo. Yield: 54.29 g (130.5 mmol; 94%).

$^1$H NMR (200 MHz, DMSO-d$_6$), δ 10.25 (s, 2H, NH), 7.61 (d, 4H, J=8.2 Hz, ArH (Ts)), 7.29 (d, 4H, J=8.0 Hz, ArH (Ts)), 7.15 (s, 1H, ArH (Ph)), 7.02 (t, 1H, J=8.1 Hz, ArH (Ph)), 6.69 (dd, 2H, J=1.8, 6.2 Hz, ArH (Ph)), 2.31 (s, 6H, CH$_3$). $^{13}$C NMR (200 MHz, DMSO-d$_6$), δ 143.24, 138.64, 136.56, 129.69, 129.59, 126.73, 114.80, 110.35, 20.95.

1,3-Dinitro-4,6-(p-toluenesulfonamido)benzene (2). To a stirring solution of acetic anhydride (100 mL) was added dropwise 70% nitric acid (15 mL) at a rate to maintain the temp below 5° C. After the addition was complete, 1,3-(p-toluenesulfamido)benzene (17 g; 40.8 mmol) was added at a rate to keep the temp below 15° C. The solution was stirred at room temperature for 12 h or overnight. The yellow precipitate was collected washed with water, and recrystallized from acetone. The mother liquor was cooled to obtain more product. Yield: 8.91 g (17.59 mmol; 43%)

$^1$H NMR (200 MHz, DMSO-d$_6$), δ 8.52 (s, 1H, ArH (Ph)), 7.78 (d, 4H, J=8.3 Hz, ArH (Ts)), 7.67 (s, 1H, ArH (Ph)), 7.41 (d, 4H, J=8.3 Hz, ArH (Ts)), 2.39 (s, 6H, CH$_3$).

1,3-Diamino-4,6-(p-toluenesulfamido)benzene (3). 1,3-Dinitro-4,6-(p-toluenesulfonamido)benzene (5.0 g; 9.9 mmol) was suspended in anhydrous ethanol (75 mL) in a pressure bomb and flushed with nitrogen. Palladium on carbon (5 wt %; 1.0 g) (A standard chemical catalyst was added quickly. The gas in the pressure bomb was alternatingly emptied via vacuum, flushed with hydrogen three times, then filled with hydrogen to 50 psi and set to shake overnight. The following morning, the reaction mixture was suctioned filtered through Celite, then washed with ethanol and acetone. The mixture was purified by dissolving in a minimal amount of acetone, then adding spatula tip amounts of sodium bicarbonate and activated charcoal, and stirring for 30 min. The solution was filtered through Celite, washed with minimal acetone, and cooled in a refrigerator overnight to precipitate the product. The product was isolated by filtration and washed with a minimal amount of cold acetone. NOTE: The compound will start to become colored if exposed to light and oxygen over a period of hours; therefore it must be stored under foil and in a vacuum. Yield: 2.35 g (5.3 mmol; 53%). $^1$H NMR (200 MHz, DMSO-d$_6$), δ 8.73 (s, 2H, NH(NH-Ts)), 7.47 (d, 4H, J=8.2 Hz, ArH (Ts)), 7.29 (d, 4H, J=8.3 Hz, ArH (Ts)), 6.31 (s, 1H, ArH (Ph)), 5.77 (s, 1H, ArH, (Ph)), 4.57 (s, 4H, NH$_2$), 2.36 (s, 6H, CH$_3$).

Poly(benzimidazolebenzophenanthroline) (BBL). Polyphosphoric acid (100 g) was deoxygenated by heating to 110° C. overnight under a flow of nitrogen with mechanical stirring. The following morning the comonomers: 1,4,5,8-naphthalene tetracarboxylic acid dianhydride (0.60 g; 2.24 mmol) and 1,3-diamino-4,6-(p-toluenesulfamido)benzene (1.0 g; 2.24 mmol) were added and heated to c. 90° C. for six hours for deprotection and formation of the tetraminobenzene monomer. The reaction was then heated to c. 180° C. for 16 h or overnight. The reaction mixture was then poured while hot into a beaker and allowed to cool to room temperature. Methanol was added, stirred manually with a glass rod, and then transferred to an Erlenmeyer flask and stirred magnetically overnight. The Teflon® stir blade has a golden film covering it. Crude yield: 1.24 g. The polymer was redissolved in methanesulfonic acid (deep burgundy red) and dropped into methanol (deep blue particles). The polymer was dried under vacuum without heat for several days.

Pyr-BBL: The free amine was generated from the 2,3,5,6-Tetramino pyridine trihydrogen chloride monohydrate by stirring the salt in polyphosphoric acid under vacuum at 80° C. Vacuum was maintained until the mixture stopped bubbling, indicating the complete release of HCl. Naphthalene dianhydride was added to the mixture and the mixture heated with stirring to 120° C. under nitrogen. After the mixture became homogeneous, the reaction temperature was increased to 185° C., and the mixture was allowed to react for 4 days with stirring. The reaction mixture was poured into water and filtered. The polymer was extracted with a soxhlet apparatus using water then methanol and dried under vacuum at 65° C.

Electrochemistry: Electrochemistry was performed on a Pine Bipotentiostat inside of a nitrogen dry box. The solvent (propylene carbonate) and supporting electrolyte were kept inside the dry box at all times. Sweep rate for cyclic voltammetry of BBL and Pyr-BBL was 100 mV/s performed on with dry propylene carbonate with EMIBTI as the supporting electrolyte. The electrochemical activity of the films was performed on BBL and Pyr-BBL films cast onto Gold button electrodes using 0.5 M solution of EMIBTI in propylene carbonate.

Type IV Devices: PProDOT was electrochemically polymerized onto a gold electrode (using a procedure described in our earlier work—Stenger-Smith, J. D.; Webber, C. K.; Anderson, N.; Chafin, A. P.; Zong, K. K.; Reynolds, J. R., *J. Electrochem. Soc.* 2002, 149, A973). The film was stored in its neutral state by applying a voltage of −0.7 V vs Ag wire. The electropolymerized PProDOT film was carefully blotted dry with lint free paper and then a drop of ethyl methyl imidazolium bis(trifluoromethylsulfonylimide) (EMI-BTI) was placed on top of the film. The cathode was made by solution co-casting 1% BBL or Pyr-BBL with 1% ionic liquid wt/wt in methane sulfonic acid. The films were dried in vacuum at 60° C. For device construction, the cathode and anode were assembled and separated with cellulose separator paper as shown in FIG. 1).

Figure 7:
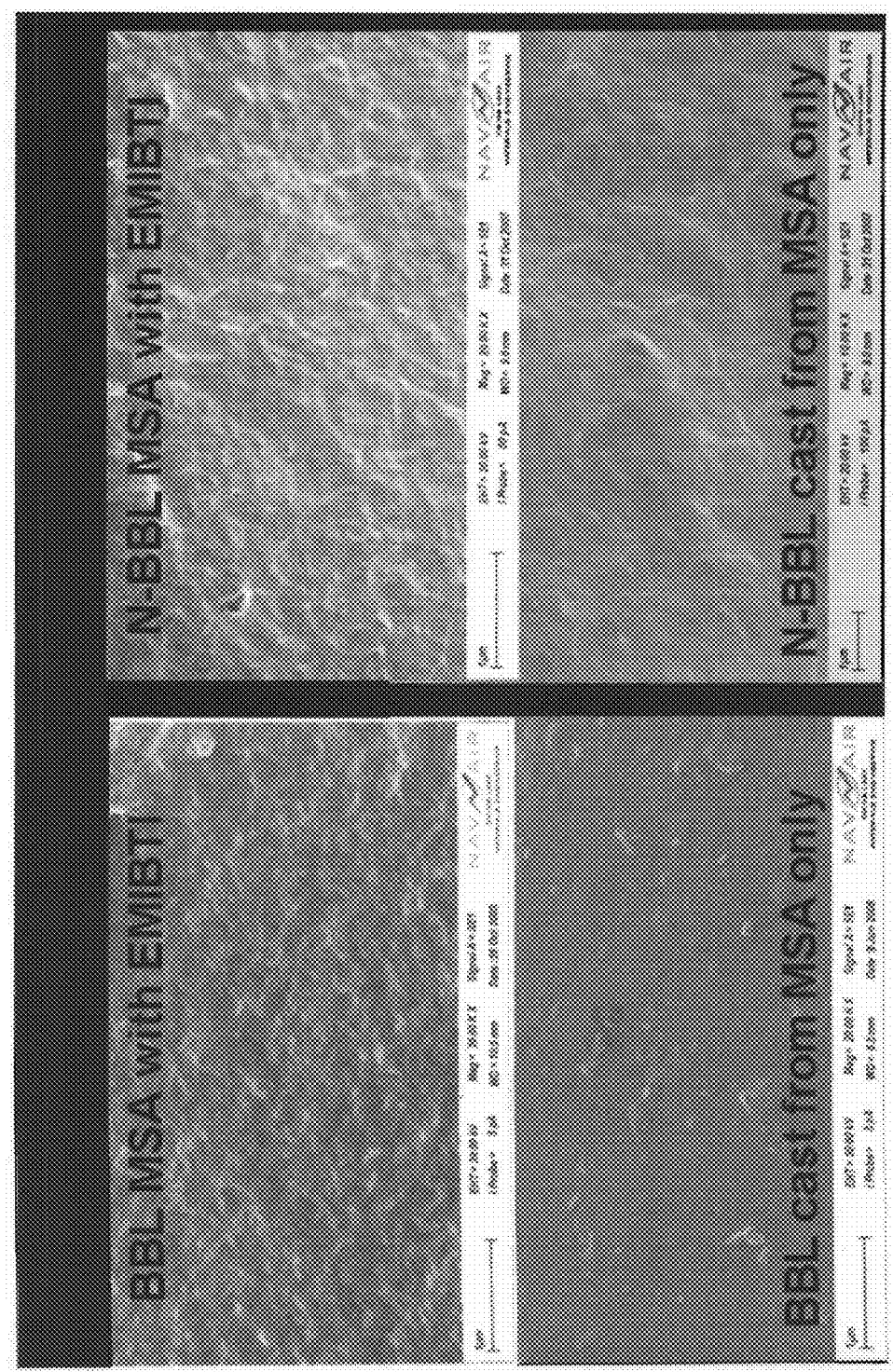
FIG. 7 is and SEM of BBL and Pyr-BBL with and without ionic liquid, according to embodiments of the invention.

In an effort to increase the initial electro-activity of BBL films, solution phase segregation was used. Instead of using a polymer to produce a semi-continuous phase of BBL, the choice was the ionic liquid EMIBTI. To prepare the solution, a concentration of 10 weight percent of a mixture having 35 weight percent BBL and 65 weight percent ionic liquid was homogenized in MSA at 90° C. under agitation for a period of ten hours. The resultant solution appeared deep red in color which phase separated upon cooling to room temperature. Presumably the de-mixing process results in two phases; one having a majority of BBL/MSA since the polymer would rather be in the presence of the acid, while the other phase is comprised mostly of ionic liquid. At 90° C. and above, the ternary mixture appeared to be isotropic and above the coexistence region of the phase diagram. The ratio of BBL to ionic liquid was carefully selected based on the estimated molecular weight of the synthesized polymer such as to optimize the ability to capture the desired morphology with a characteristic length on the order of 100 nanometers upon the phase separation triggered by MSA evaporation during the film drying process, which was carried out at 110° C. for a period of ten hours. Once the films appeared dry, they were washed in sequence with first dichloromethane followed by immersion into a methanol bath to remove the ionic liquid phase. Films fabricated via this technique had the appearance of shiny gold foil with thicknesses typically on the order of 25 microns. The same fabrication technique was utilized to generate films for morphological measurements with the exception of the substrate selection; films were cast onto plain glass slides devoid of any gold deposition. Similar processing techniques were used for Pyr-BBL films. FIG. 7 shows an SEM of BBL and Pyr-BBL with and without ionic liquid. The films cast with the ionic liquid show quite a bit more porosity and voids, which could improve the electrochemical switching properties.

Figure 8:
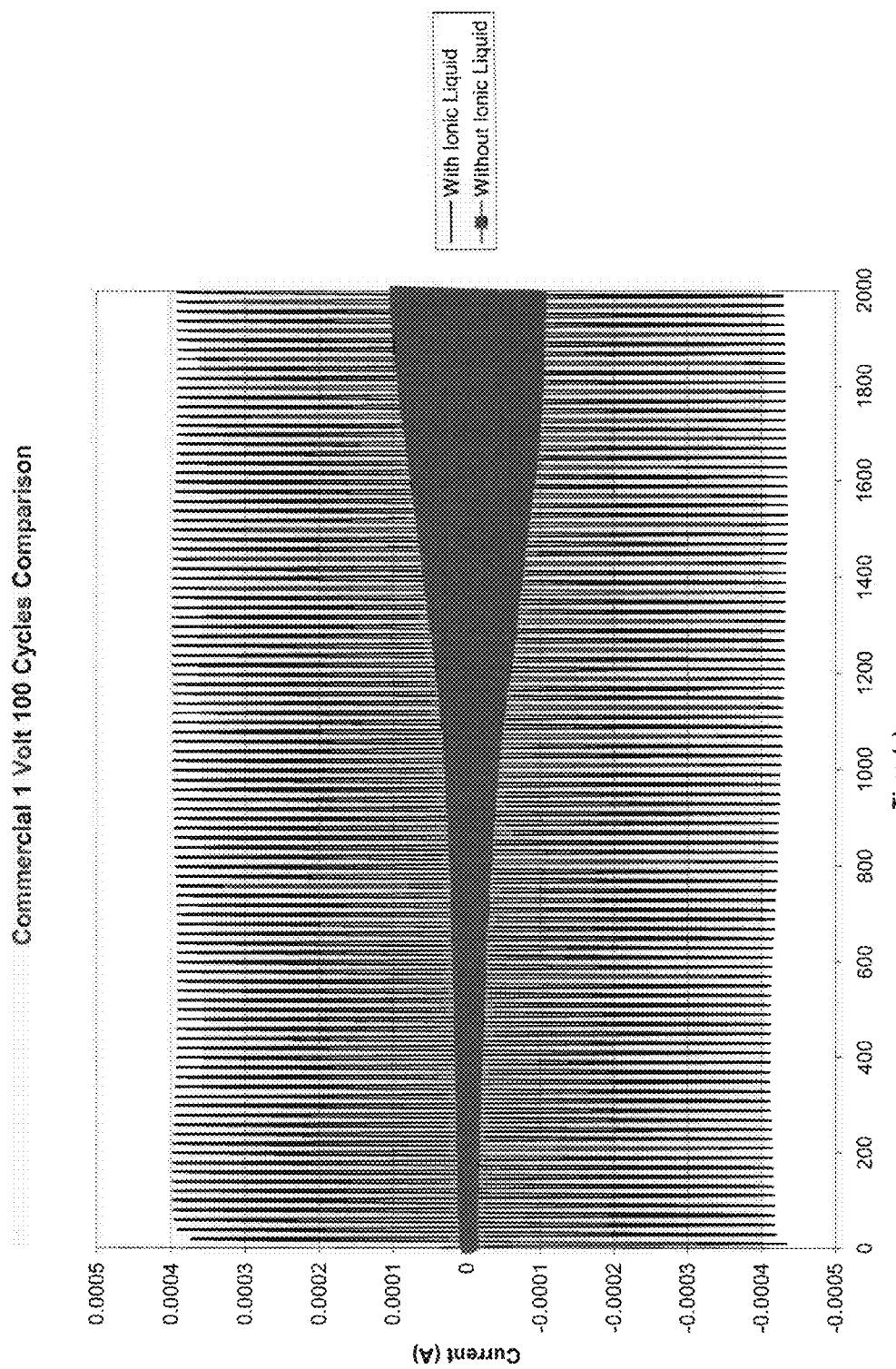
FIG. 8 is a graph showing a demonstration of current response difference between BBL cast with ionic liquid (large response) and without ionic liquid (darker smaller response), according to embodiments of the invention.
Figure 9:
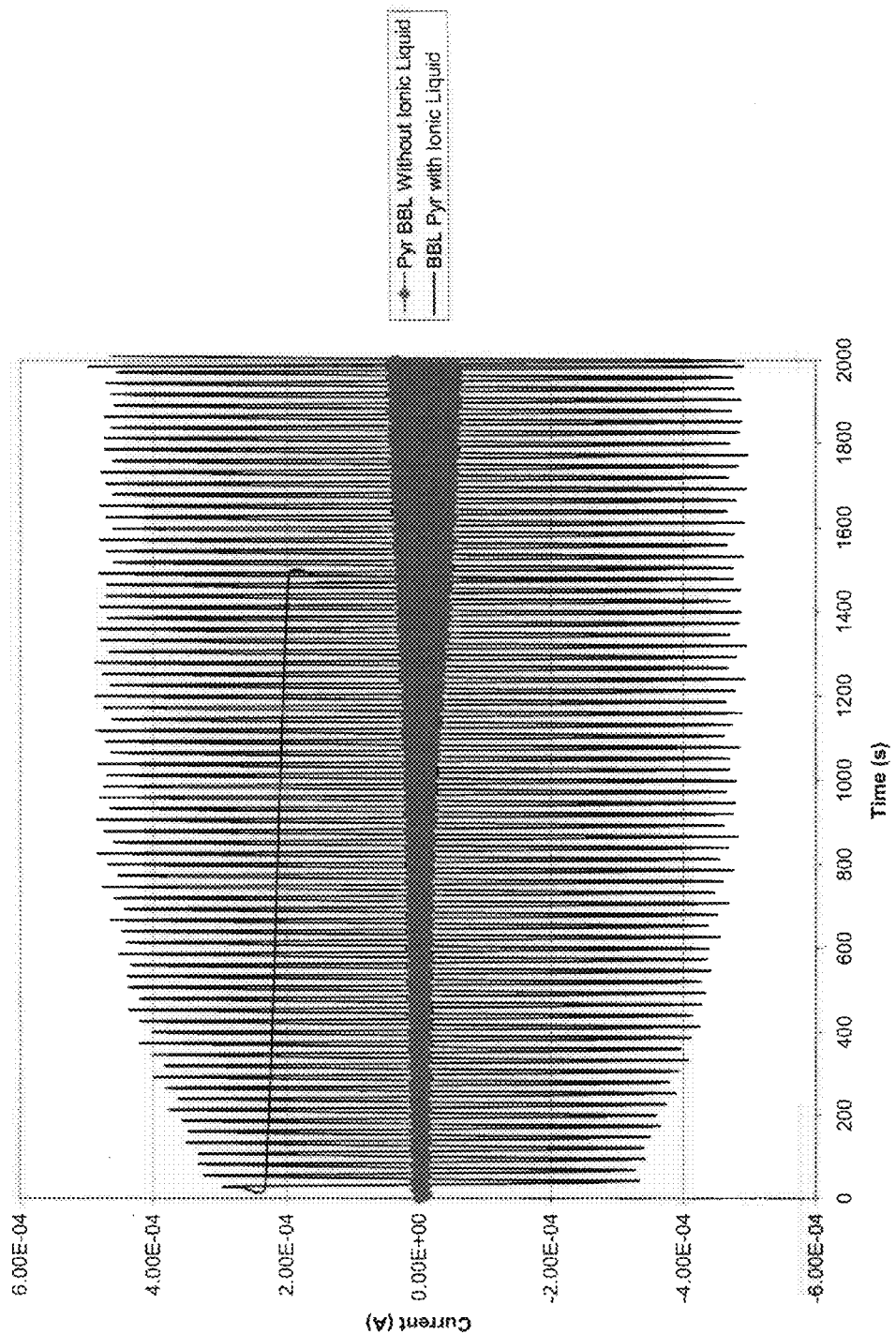
FIG. 9 is a graph showing a demonstration of current response difference between Pyr-BBL cast with ionic liquid (large response) and without ionic liquid (darker smaller response), according to embodiments of the invention.

Films were cast both with and without ionic liquids then cycled several hundred times and the current responses of the films were examined. FIG. 8 shows the difference between the current response of BBL with the ionic liquid (light) and without the ionic liquid (dark). The films cast with the ionic liquid show much more capacity and a very stable capacity over many hundreds of cycles, whereas the films cast without the ionic liquid initially show very little capacity with a gradual growing in process that leveled off after 200 cycles. After 1000 cycles the capacity of the film without the ionic liquid was about 60% of that of the capacity of the film cast with ionic liquid. Similar results were obtained with Pyr-BBL (FIG. 9).

Figure 10:
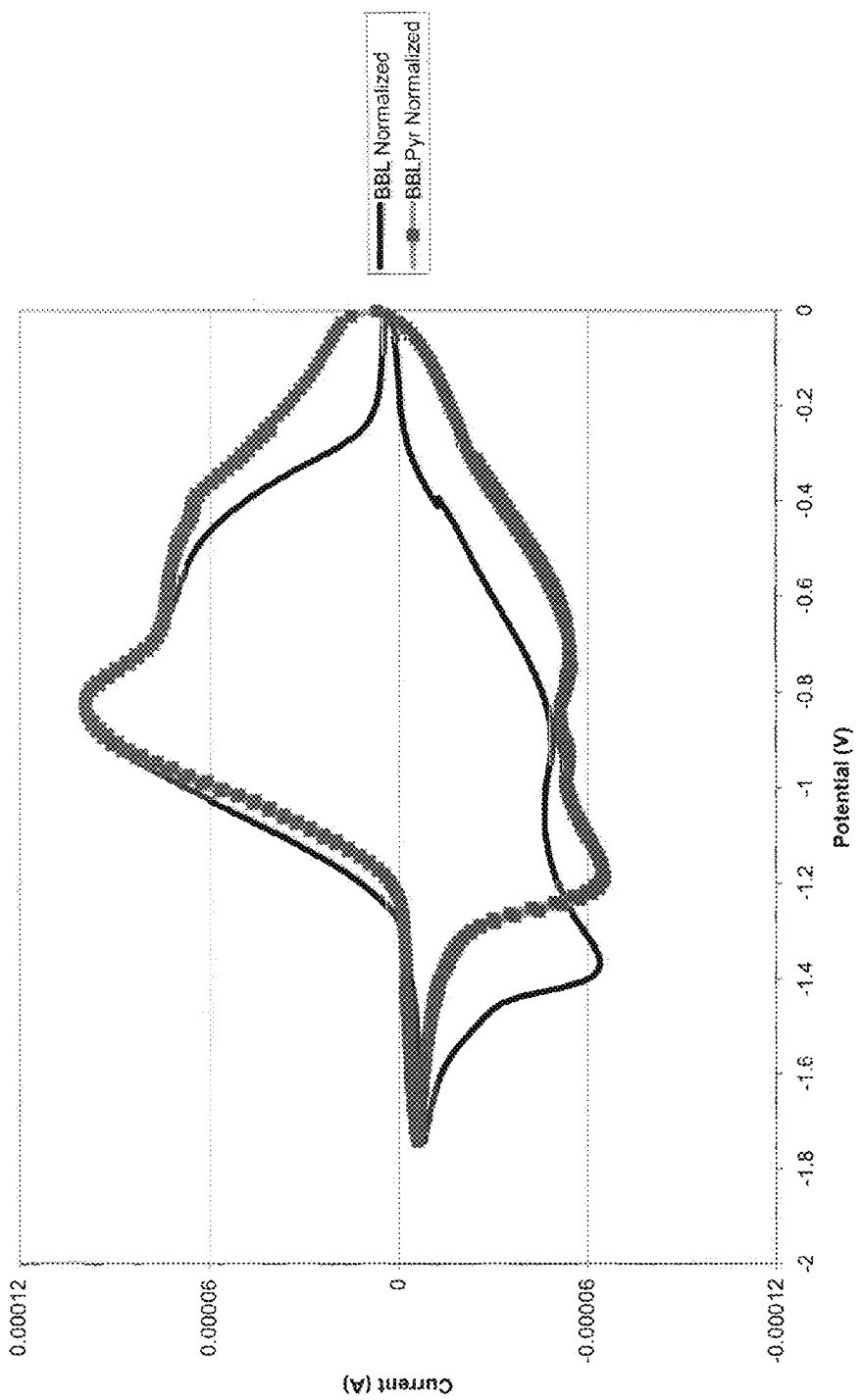
FIG. 10 is a graph of a Cyclic Voltammetry of BBL and Pyr-BBL polymers, according to embodiments of the invention.

Comparison of BBL PyrBBL Electrochemistry: With the utility of co-casting polymer films with EMIBTI established, our attention was turned to the direct comparison of BBL and Pyr-BBL. FIG. 10 shows the CV properties of BBL and Pyr-BBL. The difference in reduction potentials between BBL and Pyr-BBL was found to be 0.18V. The reduction potential for BBL and Pyr-BBL was found to be −1.18V and −1.00V respectively versus silver wire at a scan rate of 100 mV/s in EMI-BTI and propylene carbonate. The shift in reduction potential with Pyr-BBL affords a lower charging threshold signs of capacitve behavior at lower potentials.

Figure 11:
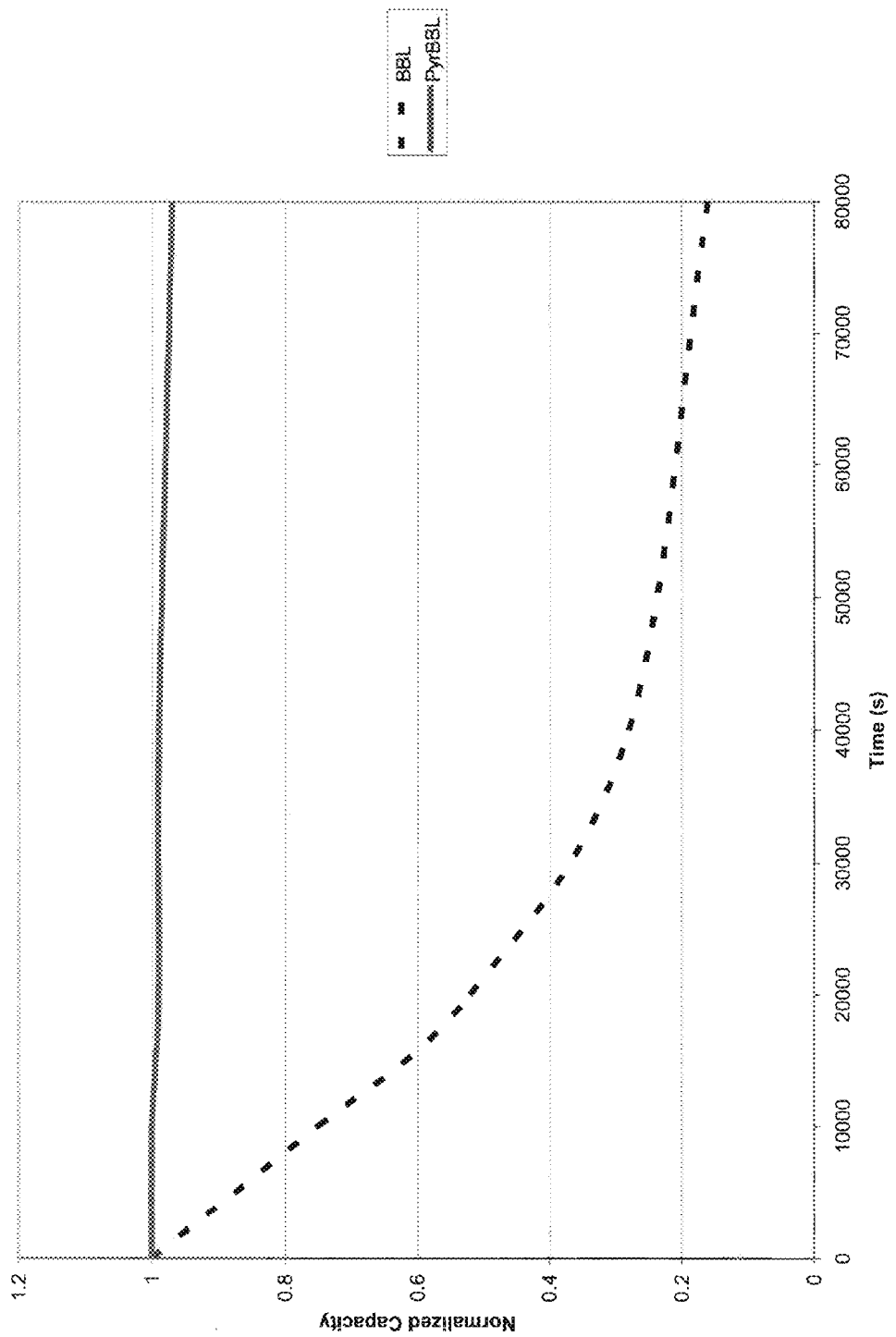
FIG. 11 is a graph showing a comparison of long term behavior of BBL and Pyr-BBL in Type IV Supercapacitors, according to embodiments of the invention.
Figure 12:
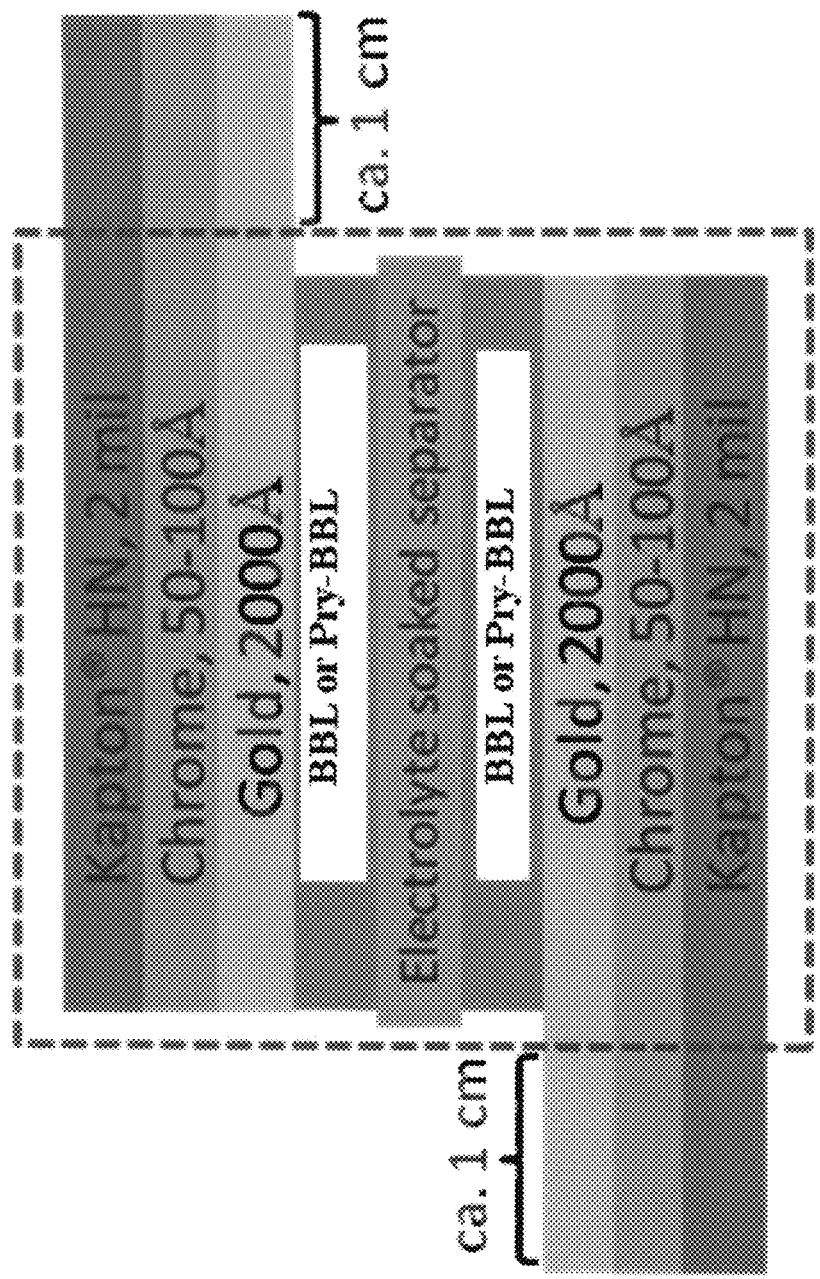
FIG. 12 is a diagram of sealed two-electrode supercapacitor construction, according to embodiments of the invention.

Comparison of BBL PyrBBL Supercapacitors: A type N supercapacitor using PProDOT and BBL was constructed and tested as was a Type N supercapacitor using PProDOT and Pyr-BBL. The long-term cycling is shown in FIG. 11. The BBL device is not very stable, as evidenced by the significant loss in charge capacity after only 1000 cycles, and the Pyr-BBL device shows excellent stability.

The use of PProDOT and PProDOT in Type I devices has shown incredible stability with a minimal loss in activity even after one hundred thousand cycles of charging and discharging. It is very unlikely that PProDOT is limiting the stability of the device. The potential that is needed to charge the device most likely approaches/exceeds the window of electrochemical stability for BBL.

To improve on the stability of the Type IV PProDOT/BBL device, BBL has to be improved upon as a cathode material. In most cases, a material becomes a better n-doper (cathode material) when the stability of the excited state is improved. The unstable nature of n-doping materials can typically be pointed to the difference in energy between the highest occupied molecular orbital (HOMO) and the lowest unoccupied molecular orbital (LUMO). The stability of n-doping materials can be therefore be improved either by lowering the energy of LUMO, raising the energy of HOMO or a combination the two.

Two common methods to lower the energy level of LUMO with respect to the energy level of the HOMO are to either increase conjugation or to introduce electron withdrawing elements. (Nenner, I.; Schulz, G. J., *J. Chem. Phys.* 1975, 62, 1747 Nenner, I.; Schulz, G. J., *J. Chem. Phys.* 1975, 62, 1747). Since BBL is a conjugated ladder polymer, tuning of the orbital energy levels will requires modifying the backbone structure of BBL to include electron withdrawing elements. The synthesis of BBL does not allow for many options for the modification of the naphthalene monomer, a substitution of pyridine for benzene in the tetramino monomer is possible, hence Pyr-BBL. This subtle change has been shown to result in an increase of electron affinity by about 0.5 eV. (Nenner, I.; Schulz, G. J., *J. Chem. Phys.* 1975, 62, 1747 Nenner, I.; Schulz, G. J., *J. Chem. Phys.* 1975, 62, 1747) The shifts in redox potentials can be used as a first order approximation of changes in energy levels of HOMO, LUMO or both. (Jerome, D.; Schulz, H. J., *Adv. Phys.* 1982, 31, 299)

Comparison of BBL and Pyr-BBL devices: For PProDOT-BBL electrochemical supercapacitors, a potential of 2.75V was required to charge the device. This is in contrast to PProDOT-Pyr-BBL supercapacitors which only require 2.00V potential to charge the device. This difference of 0.75V (0.375 in average voltage) will be a significant contributor in trading average output voltage for stability.

BBL and Pyr-BBL Tradeoff: The ability to charge the PProDOT-BBL supercapacitor at a higher potential does yield a higher average output voltage, 1.375V (maximum 2.75V) versus an average 1.00V (maximum 2.00V) output for a PProDOT-Pyr-BBL supercapacitor. But the gains in voltage are quickly lost at the expense of device stability. Cycles of charging and discharging of PProDOT-BBL supercapacitors from 0V to 2.75V over the first 2000 cycles exhibited a 25% loss of charge capacity. Along with a drop in charge capacity, coulombic efficiencies dropped from 93% to 75%. PProDOT-Pyr-BBL supercapacitors were cycled from 0V to 2.00V. After 10,000 cycles, there was 5% loss in charge capacity The coulombic efficiency of the PProDOT/Pyr-BBL devices generally remained greater than 95%.

A PProDOT-BBL supercapacitor was also run with the same testing conditions as was performed with PProDOT-Pyr-BBL, specifically the cycling between 0V and 2.00V. It was determined that the stability of the device increased somewhat, only losing 20% charge capacity after 2000 cycles, as opposed to 25%, but since the charging potential was much below that of the required threshold potential, the output voltages as well as the average current output were much lower than that of a PProDOT-Pyr-BBL device. In other words, a PProDOT-BBL device run at 2.0 volts has less capacity and is still less stable than the PProDOT-Pyr BBL device. A PProDOT/PyrBBL decays nearly catastrophically when charged to 2.75 volts.

The average current measured for a PProDOT-BBL supercapacitor was 200#A and the total capacity was 4.5 mC. The average current for PProDOT-Pyr-BBL supercapacitor was 350 μA and a total capacity of 3.3 mC. BBL has higher capacity but Pyr-BBL has higher average current suggesting faster transport.

This faster transport could be due in part to the narrowing of the HOMO-LUMO gap, as evidenced by the shift of the reduction potential by 0.18V. This lower energy barrier allows for a faster uptake and transfer of electrons, although it is also possible (but not obvious from the SEM photos) that the porosity of Pyr-BBL films is higher than the BBL films.

The PProDOT-BBL supercapacitors store about 50% more average energy than a comparable PProDOT-Pyr-BBL. The average power delivered between the two devices, are roughly equal. The PProDOT-Pyr-BBL devices are far more stable than PProDOT-BBL devices, lasting at least five times as long.

An aspect of the invention relates to an electroactive polymer-based supercapacitor including; at least two electrodes configured to store charge, where at least one electrode is an anode and at least one electrode is a cathode, where the cathode has BBL or Pry-BBL, at least one electroactive polymer associated with each electrode and/or plate, and at least two ionic liquid electrolytes, where each polymer separates the ionic liquid electrolytes from each electrode, where the mixture of at least two ionic liquid electrolytes maintains a liquid state down to −60° C.

Another aspect of the invention relates to a process used to cast films including; mixing BBL and a room temperature molten salt from a range of about 35:65 weight ratio, dissolving the mixture in about 1% methanesulfonic acid to produce a BBL solution, drop casting the solution onto glass or gold coated glass at 140° C. in air and heating for about 2 hours to produce films, drying the films in a vacuum oven at about 100° C. for at least 24 hours under dynamic vacuum, and rinsing the films to remove residual ionic liquid.

Yet another aspect of the invention relates to a process used to cast films including; mixing BBL and EMIBTI in about 35:65 weight ratio, dissolving the mixture in about 1% methanesulfonic acid to produce a BBL solution, drop casting the solution onto glass or gold coated glass at 140° C. in air and heating for about 2 hours to produce films, drying the films in a vacuum oven at about 100° C. for at least 24 hours under dynamic vacuum, and rinsing the films to remove residual ionic liquid.

In embodiments, the processes where BBL is utilized, it can be replaced with Pry-BBL. Furthermore, the processes including "rinsing" can also utilize methanol or methylene chloride.

In another aspect of the invention, the invention relates to a process to synthesize BBL including; deoxygenating polyphosphoric acid by heating to about 110° C. and stirring under a flow of nitrogen (can be mechanical stirring, can be overnight poly- (100 g)), subliming 1,4,5,8-naphthalenetetra carboxylic acid dianhydride and adding dianhydride to polyphosphoric acid to produce a first reaction mixture, adding pyridine (can be 56.1 mL; 694 mmol) to a solution of 1,3-phenylenediamine (can be 15.0 g; 139 mmol) in anhydrous dichloromethane (can be 500 mL) and cooled to about 0° C. under gas (can be any gas including nitrogen) to produce a second reaction mixture, adding p-Toluenesulfonyl chloride (can be 63.5 g; 333 mmol) portion-wise to the second reaction mixture and allowing to warm to room temperature while stirring for about 12 hours, extracting the reaction mixture with water, extracting the reaction mixture with saturated aqueous sodium bicarbonate, extracting the reaction mixture with brine to remove residual bulk water, drying the organic layer over sodium sulfate, filtering the organic layer, concentrating the organic layer in vacuo to remove majority of the organic solvent, pumping the material under high vacuum over about 48 hours, dissolving the material in ethyl acetate and extracting at least twice with 1 M aqueous hydrochloric acid, drying the material over sodium sulfate, filtering the material, and concentrating the material in vacuo, adding dropwise 70% nitric acid (can be 15 mL) at a rate to maintain the temp below 5° C. to a stirring solution of acetic anhydride (can be 100 mL), adding 1,3-(p-toluenesulfamido)benzene (can be 17 g; 40.8 mmol) to the solution at a rate to keep the temperature below 15° C., stirring the solution at room temperature for about 12 hours to about 24 hours to produce a precipitate, collecting (could be yellow) precipitate by washing with water and recrystallizing the precipitate using acetone, suspending 1,3-Dinitro-4,6-(p-toluenesulfamido)benzene (can be 5.0 g; 9.9 mmol) in anhydrous ethanol (can be 75 mL) in a pressure bomb and flushing with gas (can be any gas including nitrogen), adding palladium on carbon (can be 5 wt %; 1.0 g), emptying the gas in the pressure bomb via vacuum and flushing with a gas (can be any gas including hydrogen) at least three times, filling the pressure bomb with gas (can be any gas including hydrogen) to 50 psi and shaking the suspension, suction-filtering the reaction mixture through Celite and washing with ethanol and acetone, purifying the mixture by dissolving in a minimal amount of acetone and adding spatula tip amounts of sodium bicarbonate and activated charcoal and stirring for about 30 minutes to produce a solution, filtering the solution through Celite, washing with an effective amount of acetone, and cooling the solution in refrigeration for an effective amount of time to precipitate a product, isolating the product by filtering and washing with an effective amount of cold acetone, protecting the product from light exposure, adding to the product 1,4,5,8-naphthalenetetracarboxylic acid dianhydride and 1,3-diamino-4,6-(p-toluenesulfonamido)benzene and adding to polyphosphoric acid (PPA) at 90° C. for about 6 hours to produce a reaction mixture, increasing temperature to the reaction mixture temperature to 180° C., and holding at the temperature for about 16 hours, cooling the reaction mixture and precipitating in methanol to produce a residue, dissolving the residue in methanesulfonic acid (MSA) and reprecipitating in methanol at least twice to produce a polymer, and drying the polymer under vacuum without applying heat for about a week. The BBL processed above can be formed into films for use in supercapacitor(s). The BBL processed above can be formed into film for depositing high surface area for the use in supercapacitor(s).

Still yet another aspect of the invention relates to a process to synthesize Pyr-BBL including; deoxygenating polyphosphoric acid (can be 100 g) by heating to 110° C. for an effective amount of time under a flow of gas (can be any gas including nitrogen) and stirring (can be mechanical stirring), subliming 1,4,5,8-naphthalenetetracarboxylic acid dianhydride adding the dianhydride to the polyphosphoric acid to produce a first reaction mixture, obtaining 2,3,5,6-tetramino pyridine trihydrogen chloride monohydrate by the reduction of 2,6-diamino-3,5-dinitro pyridine with $Sn^0$ and aqueous HCl, generating free amines from 2,3,5,6-tetramino pyridine trihydrogen chloride monohydrate by stirring a salt in polyphosphoric acid under vacuum at about 80° C., maintaining vacuum until the mixture stopped bubbling which indicates the complete release of HCl, adding 1,4,5,8-naphthalenetetracarboxylic acid dianhydride the mixture, heating and stirring the mixture to about 120° C. under gas (can be any gas including nitrogen), increasing temperature to the mixture after becoming homogeneous to about 185° C., stirring the mixture for about 4 days, poring the reaction mixture into water and filtering the mixture to produce a polymer, and extracting the polymer with a soxhlet apparatus using water then methanol and drying under vacuum at about 65° C. for about 2 days. The Pyr-BBL processed above can be formed into films for use in supercapacitor(s). The Pyr-BBL processed above can be formed into film for depositing high surface area for the use in supercapacitor(s).

In embodiments, the supercapacitor including electroactive polymer(s) is in the form of a film. Embodiments, the supercapacitor having electroactive polymer(s) includes at least one of PProDOT. Embodiments, the supercapacitor having electroactive polymer(s) includes at least one of PEDOT.

In embodiments including the electrolyte it can be a 50:50 mixture of EMIBTI and EMIPF6. In other embodiments, the electrolyte includes at least one imidazolium group:

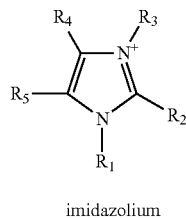

imidazolium where R1 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms; where R2 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms, where R3 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms, where R4 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms, and where R5 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms.

Embodiments with the supercapacitor having a dielectric layer, it includes ionic liquid electrolytes comprises at least one of EMIBTI/TEABTI, EMIBTI/EMIBF4, EMIBTI/TEABF4, EMIBTI/TBAP, EMIMS, and PolyetherIBTI. In other embodiments, the weight percentage of EMIBTI in the electrolyte mixture in the ranges from about 5% to about 95% by weight. Yet in other embodiments, the weight percentage of EMIPF6 in the electrolyte mixture in the ranges from about 5% to about 95% by weight.

Embodiments of the invention include an ionic electrolyte mixture in the ranges of about 50% to about 50% by weight. In other embodiments, the ionic liquid electrolytes are EMIBTI/EMIBF4. In yet other embodiments, the ionic electrolyte mixture in the ranges of about 5% to about 95% by weight. Still yet in other embodiments, the ionic electrolyte mixture in the ranges of about 95% to about 5% by weight. In embodiments, the electrode(s) are made of effective material(s) which includes at least one of polyimide(s), metal, metal alloys, and any combination of like-conductive material(s) thereof.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. An electroactive polymer-based supercapacitor, comprising:
    at least two electrodes configured to store charge, wherein at least one electrode is an anode and at least one electrode is a cathode, wherein said cathode having BBL or Pry-BBL;
    at least one electroactive polymer associated with each said electrode; and
    at least two ionic liquid electrolytes, wherein each said polymer separates said ionic liquid electrolytes from each said electrode, wherein said mixture of at least two ionic liquid electrolytes maintains a liquid state down to −60° C.

2. The supercapacitor according to claim 1, wherein said electroactive polymer is in the form of a film.

3. The supercapacitor according to claim 1, wherein said electrolyte is a 50:50 mixture of EMIBTI and EMIPF6.

4. The supercapacitor according to claim 1, wherein said supercapacitor having a dielectric layer including said ionic liquid electrolytes comprises at least one of EMIBTI/TEABTI, EMIBTI/EMIBF4, EMIBTI/TEABF4, EMIBTI/TBAP, EMIMS, and PolyetherIBTI.

5. The supercapacitor according to claim 1, wherein the weight percentage of EMIBTI in the electrolyte mixture in the ranges from about 5% to about 95% by weight.

6. The supercapacitor according to claim 1, wherein the weight percentage of EMIPF6 in the electrolyte mixture in the ranges from about 5% to about 95% by weight.

7. The supercapacitor according to claim 1, wherein said ionic electrolyte mixture in the ranges of about 50% to about 50% by weight.

8. The supercapacitor according to claim 1, wherein said electrode(s) are made of effective material(s) which comprises at least one of polyimide(s), metal, metal alloys, and any combination of like-conductive material(s) thereof.

9. The supercapacitor according to claim 1, wherein said electroactive polymer(s) which comprises at least one of PProDOT.

10. The supercapacitor according to claim 1, wherein said electroactive polymer(s) which comprises at least one of PEDOT.

11. The supercapacitor according to claim 1, wherein said ionic liquid electrolytes is EMIBTI/EMIBF4.

12. The supercapacitor according to claim 1, wherein said ionic electrolyte mixture in the ranges of about 5% to about 95% by weight.

13. The supercapacitor according to claim 1, wherein said ionic electrolyte mixture in the ranges of about 95% to about 5% by weight.

14. The supercapacitor according to claim 1, wherein said ionic electrolyte mixture in the ranges of gout 50% to about 50% by weight.

15. The supercapacitor according to claim 1, wherein said electrolyte includes at least one imidazolium group:

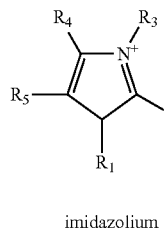

imidazolium wherein R1 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms;

wherein R2 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms;

wherein R3 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms;

wherein R4 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from to 22 carbon atoms; amino; sulfonate groups; silyl; and, perfluoro alky including from 1 to about 22 carbon atoms; and wherein R5 is substituents selected from the group including of hydrogen; alkyl of from 1 to about 22 carbon atoms; alkoxy including from 1 to about 22 carbon atoms; nitro; halogen; cyano ester, mono- and di-alkylamine of from 1 to about 22 carbon atoms; ester groups including from 1 to about 22 carbon atoms; amide including from 1 to 22 carbon atoms; alcohol including from 1 to 22 carbon atoms; amino; sulfonate groups; silyl; and, perfluoro alky including from 1 to about 22 carbon atoms.

* * * * *